United States Patent

Schoening et al.

(10) Patent No.: US 9,328,218 B2
(45) Date of Patent: May 3, 2016

(54) POLYGLYCOL BIS-[3-(7-TERT-BUTYL-2-OXO-3-PHENYL-3H-BENZOFURAN-5-YL-)PROPANOYL] DERIVATIVES AS STABILIZERS OF ORGANIC MATERIAL

(71) Applicant: BASF SE, Ludwigshafen (DE)

(72) Inventors: Kai-Uwe Schoening, Oberwil (CH); Cinzia Tartarini, Basel (CH); Walid Al-Akhdar, Oberwil (CH); Ulrich Berens, Binzen (DE); Bruno Rotzinger, Delemont (CH); Alexander Dichtl, Loerrach (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/410,979

(22) PCT Filed: Jul. 9, 2013

(86) PCT No.: PCT/EP2013/064469
§ 371 (c)(1),
(2) Date: Dec. 23, 2014

(87) PCT Pub. No.: WO2014/009361
PCT Pub. Date: Jan. 16, 2014

(65) Prior Publication Data
US 2015/0191581 A1    Jul. 9, 2015

Related U.S. Application Data

(60) Provisional application No. 61/671,136, filed on Jul. 13, 2012.

(30) Foreign Application Priority Data

Jul. 13, 2012    (EP) .................................... 12176407

(51) Int. Cl.
| C08K 5/15 | (2006.01) |
| A61L 24/00 | (2006.01) |
| C09K 3/00 | (2006.01) |
| C07D 307/00 | (2006.01) |
| C08K 5/1535 | (2006.01) |

(Continued)

(52) U.S. Cl.
CPC ............ C08K 5/1535 (2013.01); C07D 307/83 (2013.01); C08K 5/05 (2013.01); C08K 5/17 (2013.01); C08K 5/52 (2013.01); C08K 5/5393 (2013.01)

(58) Field of Classification Search
None
See application file for complete search history.

(56) References Cited

U.S. PATENT DOCUMENTS

| 4,325,863 A | 4/1982 | Hinsken et al. |
| 4,338,244 A | 7/1982 | Hinsken et al. |

(Continued)

FOREIGN PATENT DOCUMENTS

| EP | 0 423 070 A2 | 4/1991 |
| WO | WO 80/01566 A1 | 8/1980 |

(Continued)

OTHER PUBLICATIONS

International Search Report issued Aug. 16, 2013 in PCT/EP2013/064469.

(Continued)

*Primary Examiner* — Susannah Chung
*Assistant Examiner* — Robert T Butcher
(74) *Attorney, Agent, or Firm* — Oblon, McClelland, Maier & Neustadt, L.L.P

(57) ABSTRACT

The invention relates to a compound of the formula (I-1)

wherein
n is 1, 2, 3, 4, 5, 6, 7, 8, 9, 10, 11, 12, 13, 14, 15, 16, 17, 18, 19, 20, 21, 22, 23, 24 or 25, $R_1$, $R_2$, $R_3$, $R_4$, $R_5$, $R'_1$, $R'_2$, $R'_3$, $R'_4$ and $R'_5$ are each independently from each other H or $C_1$-$C_8$-alkyl. Compounds of the formula (I-1) or stabilizer mixtures containing compounds of the formula (I-1) are especially used for stabilization of polymers against degradation by oxidation, heat or light.

14 Claims, No Drawings

(51) Int. Cl.
*C07D 307/83* (2006.01)
*C08K 5/05* (2006.01)
*C08K 5/17* (2006.01)
*C08K 5/52* (2006.01)
*C08K 5/5393* (2006.01)

(56) References Cited

U.S. PATENT DOCUMENTS

| | | | |
|---|---|---|---|
| 4,611,016 | A | 9/1986 | Hinsken et al. |
| 7,060,425 | B1 * | 6/2006 | Jeganathan et al. ........... 430/543 |
| 7,763,184 | B2 * | 7/2010 | Su et al. ........................ 252/401 |
| 2009/0012192 | A1 | 1/2009 | Jacobs et al. |
| 2013/0207043 | A1 | 8/2013 | Menozzi et al. |
| 2014/0058021 | A1 | 2/2014 | Fischer et al. |
| 2015/0087755 | A1 | 3/2015 | Hoelzl et al. |

FOREIGN PATENT DOCUMENTS

| | | |
|---|---|---|
| WO | WO 00/23849 A1 | 4/2000 |
| WO | WO 2012/052377 A1 | 4/2012 |
| WO | WO 2012/150527 A1 | 11/2012 |
| WO | WO 2013/139799 A1 | 9/2013 |
| WO | WO 2014/009361 A1 | 1/2014 |
| WO | WO 2015/004580 A1 | 1/2015 |

OTHER PUBLICATIONS

European Search Report issued Sep. 20, 2012 in Patent Application No. 12 17 6407.

* cited by examiner

POLYGLYCOL BIS-[3-(7-TERT-BUTYL-2-OXO-3-PHENYL-3H-BENZOFURAN-5-YL-)PROPANOYL] DERIVATIVES AS STABILIZERS OF ORGANIC MATERIAL

Organic materials are susceptible to degradation, which can be induced by heat, light and/or oxidation. For reducing such degradation, numerous solutions in regard to an incorporation or addition of a stabilizer are proposed.

Furthermore, in order to meet the fire resistance requirements in force on the market place for final goods used in different industries like furniture and bedding, the use of flame retardants is necessary. For example, the typically used flame retardants for flexible foams, especially polyurethane foams, are chlorinated, brominated or halogen free flame retardants. For polyol, which is a typical starting material for polyurethane, it is known that its oxidation resistance is generally affected by the presence of a flame retardant.

US-A-2009/0012192 discloses the use of a group of benzofuran-2-one derivatives as a stabilizer for polyurethane foams containing colorants and organohalogen (i.e. haloorganic) flame retardants.

WO-A-1980/01566 discloses benzofuran-2-onic or indolin-2-onic compounds as stabilizers of polymers. Inter alia, the provided genus of benzofuran-2-one derivatives comprises also several subgroups of derivatives, which comprise two structural benzofuran-2-one units. A disclosed example for one of these subgroups is 10-[3-(2-oxo-3-phenyl-3H-benzofuran-5-yl)propanoyloxy]decyl 3-(2-oxo-3-phenyl-3H-benzofuran-5-yl)propanoate [No. 26] as depicted:

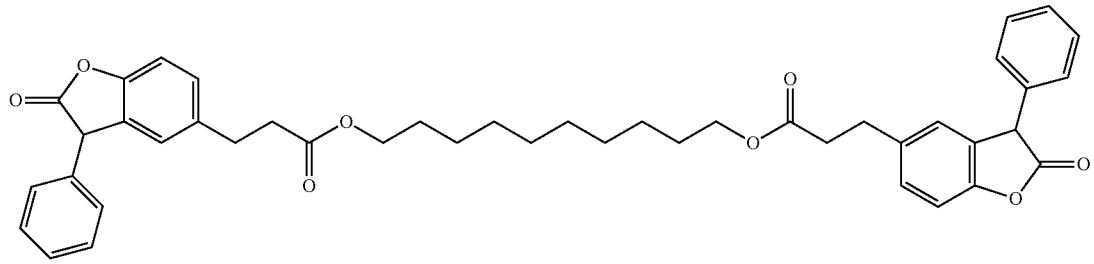 [SMILES: O=C(CCc1ccc2c(c1)C(c1ccccc1)C(=O)O2)OCCCCCCCCCCOC(=O)CCc1ccc2c(c1)C(c1ccccc1)C(=O)O2]

This compound is applied in styrene-butadiene rubber at example 17. The compound is synthesized via the reaction of mandelic acid with a 3-(4-hydroxyphenyl)propionic acid diester.

WO-A-2000/23849 discloses benzofuranoic compounds in colour photographic material as scavengers of the oxidized form of the developer, especially when contained in an interlayer between light sensitive layers. Inter alia, the provided genus of benzofuran-2-one derivatives comprises several subgroups of bis-(benzofuran-2-one) derivatives. A disclosed example for one of these subgroups is 6-[3-(7-tert-butyl-2-oxo-3-phenyl-3H-benzofuran-5-yl)propanoyloxy]hexyl 3-(7-tert-butyl-2-oxo-3-phenyl-3H-benzofuran-5-yl)propanoate [No. 19] as depicted:

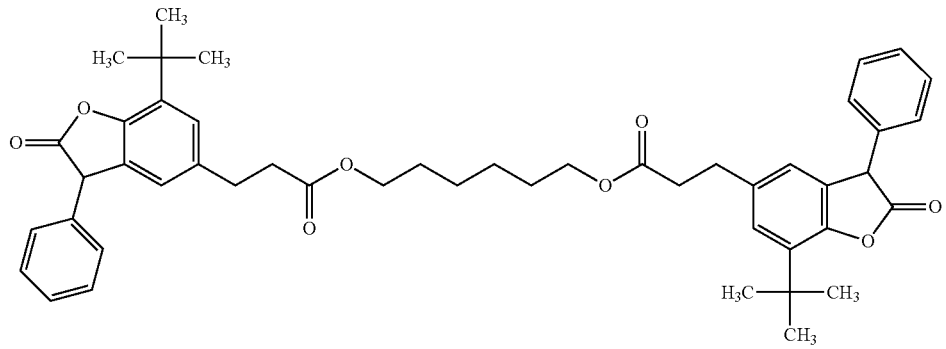 [SMILES: CC(C)(C)c1cc(CCC(=O)OCCCCCCOC(=O)CCc2cc3c(c(C(C)(C)C)c2)OC(=O)C3c2ccccc2)cc2c1OC(=O)C2c1ccccc1]

This compound is applied at example 3/test element 25 in a layer, which comprises also gelatin, tricresyl phosphate and the sodium salt of 2-sulphonate-4,8-disobutyl-naphthalene. The compound is synthesized in two steps at example 11, i.e. reaction of 3-(3-tert-butyl-4-hydroxy-phenyl)propionic acid with mandelic acid and afterwards diesterification of the obtained propionic acid derivative with 1,6-hexanediol.

There is still a need for further technical solutions towards stabilization of organic material against the detrimental impact of heat, light and/or oxidation.

It has now been found that a specific group of polyglycol bis-[3-(7-tert-butyl-2-oxo-3-phenyl-3H-benzofuran-5-yl-)propanoyl]derivatives is suitable for stabilization of organic material against degradation by heat, light and/or oxidation.

The present invention relates to a compound of formula (I-1)

(I-1)

wherein
n is 1, 2, 3, 4, 5, 6, 7, 8, 9, 10, 11, 12, 13, 14, 15, 16, 17, 18, 19, 20, 21, 22, 23, 24 or 25, $R_1$, $R_2$, $R_3$, $R_4$, $R_5$, $R'_1$, $R'_2$, $R'_3$, $R'_4$ and $R'_5$ are each independently from each other H or $C_1$-$C_8$-alkyl.

A compound of formula (I-1) possesses at least two asymmetric carbon atoms, i.e. the carbon atoms at the 3-positions of the benzofuran-2-one rings, which results in enantiomers or diastereomers. The Invention relates to any one of these enantiomers, mixtures of enantiomers, diastereomers or mixtures of diastereomers.

$C_1$-$C_8$-alkyl is linear or branched and for example methyl, ethyl, n-propyl, 1-methylethyl, n-butyl, 1-methylpropyl, 2-methylpropyl, 1,1-dimethylethyl, n-pentyl, 1-methylbutyl, 3-methylbutyl, n-hexyl, 1-methylpentyl, 2-methylpentyl, 4-methylpentyl, 2-ethyl-butyl, n-heptyl, 1-methylhexyl, n-octyl, 1-methylheptyl, 2-ethylhexyl, 5,5-dimethylhexyl or 1,1,3,3-tetramethylbutyl. Preferred is $C_1$-$C_4$-alkyl and $C_8$-alkyl, in particular methyl, ethyl, 1-methylethyl, 1,1-dimethylethyl and 1,1,3,3-tetramethylbutyl, especially methyl, 1,1-dimethylethyl and 1,1,3,3-tetramethylbutyl.

Preferred is a compound of the formula (I-1), wherein $R_1$ to $R_5$ and $R'_1$ to $R'_5$ are H.

Preferred is a compound of the formula (I-1), wherein
n is 1, 2, 3, 4, 5, 6, 7, 8, 9, 10, 11, 12, 13, 14, 15, 16, 17, 18, 19, 20, 21, 22, 23, 24 or 25, $R_1$, $R_2$, $R_3$, $R_4$, $R_5$, $R'_1$, $R'_2$, $R'_3$, $R'_4$ and $R'_5$ are each independently from each other H or E, and E is $C_1$-$C_8$-alkyl.

Preferred is a compound of the formula (I-1), wherein $R_1$, $R_2$, $R_3$, $R_4$, $R_5$, $R'_1$, $R'_2$, $R'_3$, $R'_4$ and $R'_5$ are each independently from each other H or $C_1$-$C_8$-alkyl, with the proviso that at least one of $R_1$ to $R_5$ and at least one of $R'_1$ to $R'_5$ is $C_1$-$C_8$-alkyl.

Preferred is a compound of the formula (I-1), wherein $R_1$, $R_2$, $R_3$, $R_4$, $R_5$, $R'_1$, $R'_2$, $R'_3$, $R'_4$ and $R'_5$ are each independently from each other H or E, and E is $C_1$-$C_8$-alkyl, with the proviso that at least one of $R_1$ to $R_5$ and at least one of $R'_1$ to $R'_5$ is E.

Preferred is a compound of the formula (I-1), wherein $R_1$ is different to $R'_1$, $R_2$ is different to $R'_2$, $R_3$ is different to $R'_3$, $R_4$ is different to $R'_4$, or $R_5$ is different to $R'_5$.

Preferred is a compound of the formula (I-1), wherein E is $C_1$-$C_8$-alkyl and $R_1$ is different to $R'_1$, $R_2$ is different to $R'_2$, $R_3$ is different to $R'_3$, $R_4$ is different to $R'_4$, or $R_5$ is different to $R'_5$.

Preferred is a compound of the formula (I-1), wherein
$R_1$ or $R_5$ is H and $R'_1$ or $R'_5$ is H; and
$R_1$ is different to $R'_1$, $R_2$ is different to $R'_2$, $R_3$ is different to $R'_3$, $R_4$ is different to $R'_4$, or
$R_5$ is different to $R'_5$.

Preferred is a compound of the formula (I-1), wherein E is $C_1$-$C_8$-alkyl;
$R_1$ or $R_5$ is H and $R'_1$ or $R'_5$ is H; and
$R_1$ is different to $R'_1$, $R_2$ is different to $R'_2$, $R_3$ is different to $R'_3$, $R_4$ is different to $R'_4$, or
$R_5$ is different to $R'_5$.

Preferred is a compound of the formula (I-1), wherein
$R_1$ or $R_5$ is H and $R'_1$ or $R'_5$ is H;
$R_1$ is different to $R'_1$, $R_2$ is different to $R'_2$, $R_3$ is different to $R'_3$, $R_4$ is different to $R'_4$, or $R_5$ is different to $R'_5$; and
at least one of $R_1$ to $R_5$ and at least one of $R'_1$ to $R'_5$ is $C_1$-$C_4$-alkyl; in particular two of $R_1$ to $R_5$ and two of $R_1$ to $R_5$ are $C_1$-$C_4$-alkyl.

Preferred is a compound of the formula (I-1), wherein E is $C_1$-$C_8$-alkyl;
$R_1$ or $R_5$ is H and $R'_1$ or $R'_5$ is H;
$R_1$ is different to $R'_1$, $R_2$ is different to $R'_2$, $R_3$ is different to $R'_3$, $R_4$ is different to $R'_4$, or $R_5$ is different to $R'_5$; and
at least one of $R_1$ to $R_5$ and at least one of $R'_1$ to $R'_5$ is $C_1$-$C_4$-alkyl; in particular two of $R_1$ to $R_5$ and two of $R_1$ to $R_5$ are $C_1$-$C_4$-alkyl.

Preferred is a compound of the formula (I-1), wherein n is an integer of 1 to 9, in particular 1, 2, 3, 4, 5 or 6, especially 2, 3, 4, 5 or 6 and very especially 2, 3 or 4.

Preferred is a compound of the formula (I-1), wherein $C_1$-$C_8$-alkyl is selected from the group consisting of $C_1$-$C_4$-alkyl and $C_8$-alkyl, in particular methyl, ethyl, 1-methylethyl, 1,1-dimethylethyl and 1,1,3,3-tetramethylbutyl Preferred is a compound of the formula (I-1), wherein E is $C_1$-$C_4$-alkyl or $C_8$-alkyl, in particular methyl, ethyl, 1-methylethyl, 1,1-dimethylethyl or 1,1,3,3-tetramethylbutyl.

Preferred is a compound of the formula (I-1), wherein n is an integer of 1 to 9.

Preferred is a compound of the formula (I-1), wherein n is an integer of 1 to 9 and E is $C_1$-$C_4$-alkyl or $C_8$-alkyl.

Preferred is a compound of the formula (I-1), wherein
$R_1$ or $R_5$ is H and $R'_1$ or $R'_5$ is H;
$R_1$ is different to $R'_1$, $R_2$ is different to $R'_2$, $R_3$ is different to $R'_3$, $R_4$ is different to $R'_4$, or $R_5$ is different to $R'_5$; and
at least one of $R_1$ to $R_5$ and at least one of $R'_1$ to $R'_5$ is $C_1$-$C_4$-alkyl; in particular two of $R_1$ to $R_5$ and two of $R_1$ to $R_5$ are $C_1$-$C_4$-alkyl.

Preferred is a compound of the formula (I-1), wherein E is $C_1$-$C_4$-alkyl or $C_8$-alkyl;
$R_1$ or $R_5$ is H and $R'_1$ or $R'_5$ is H;
$R_1$ is different to $R'_1$, $R_2$ is different to $R'_2$, $R_3$ is different to $R'_3$, $R_4$ is different to $R'_4$, or $R_5$ is different to $R'_5$; and
at least one of $R_1$ to $R_5$ and at least one of $R'_1$ to $R'_5$ is $C_1$-$C_4$-alkyl; in particular two of $R_1$ to $R_5$ and two of $R_1$ to $R_5$ are $C_1$-$C_4$-alkyl.

Preferred is a compound of the formula (I-1), wherein n is an integer of 1 to 9;
$R_1$ or $R_5$ is H and $R'_1$ or $R'_5$ is H;
$R_1$ is different to $R'_1$, $R_2$ is different to $R'_2$, $R_3$ is different to $R'_3$, $R_4$ is different to $R'_4$, or $R_5$ is different to $R'_5$; and
at least one of $R_1$ to $R_5$ and at least one of $R'_1$ to $R'_5$ is $C_1$-$C_4$-alkyl; in particular two of $R_1$ to $R_5$ and two of $R_1$ to $R_5$ are $C_1$-$C_4$-alkyl.

Preferred is a compound of the formula (I-1), wherein n is an integer of 1 to 9;
E is $C_1$-$C_4$-alkyl or $C_8$-alkyl;
$R_1$ or $R_5$ is H and $R'_1$ or $R'_5$ is H;
$R_1$ is different to $R'_1$, $R_2$ is different to $R'_2$, $R_3$ is different to $R'_3$, $R_4$ is different to $R'_4$, or $R_5$ is different to $R'_5$; and
at least one of $R_1$ to $R_5$ and at least one of $R'_1$ to $R'_5$ is $C_1$-$C_4$-alkyl; in particular two of
$R_1$ to $R_5$ and two of $R_1$ to $R_5$ are $C_1$-$C_4$-alkyl.

A further embodiment of the invention is a stabilizer mixture [I-1/2/3], which comprises
b-I-1) a compound of formula (I-1);
b-I-2) a compound of formula (I-2)

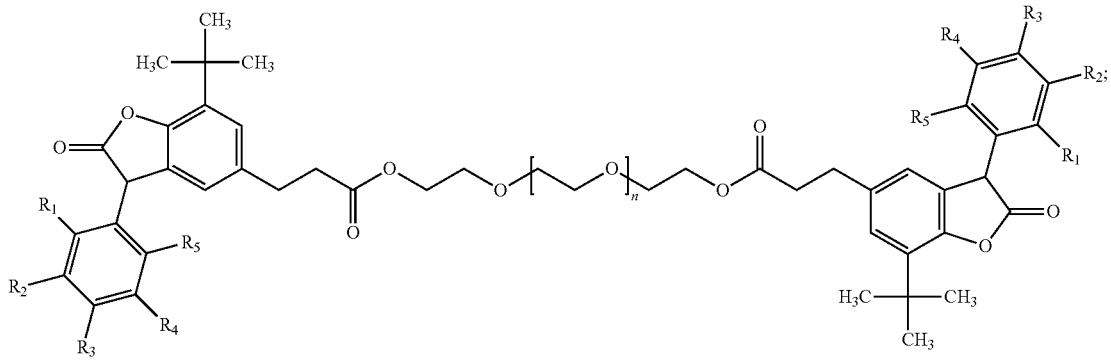

and
b-I-3) a compound of formula (I-3)

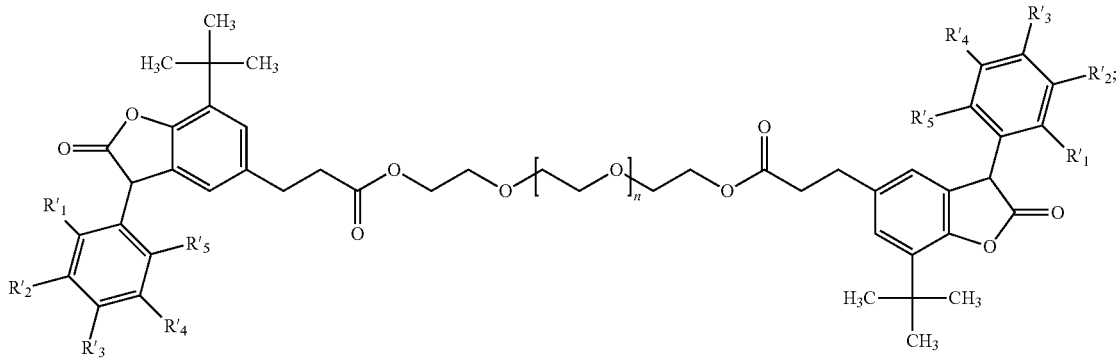

wherein n, $R_1$ to $R_5$ and $R'_1$ to $R'_5$ are defined as described at the embodiment of the compound of formula (I-1); and $R_1$ is different to $R'_1$, $R_2$ is different to $R'_2$, $R_3$ is different to $R'_3$, $R_4$ is different to $R'_4$, or $R_5$ is different to $R'_5$.

The preferences and combination of preferences for n, $R_1$ to $R_5$, $R'_1$ to $R'_5$ and E, which are described at the embodiment of the compound of the formula (I-1), apply similarly to the stabilizer mixture [I-1/2/3] under the exception of the preference that $R_1$ to $R_5$ and $R'_1$ to $R'_5$ are H.

Preferred is a stabilizer mixture [I-1/2/3], wherein the weight ratio between the compound of the formula (I-1) and the compound of the formula (I-2) is from 0.1 to 10 and the weight ratio between the compound of the formula (I-1) and the compound of the formula (I-3) is from 0.01 to 100.

A further embodiment of the invention is a stabilizer mixture [I-1-II-1], which comprises b-I-1) a compound of formula (I-1); and b-II-1) a compound of formula (II-1)

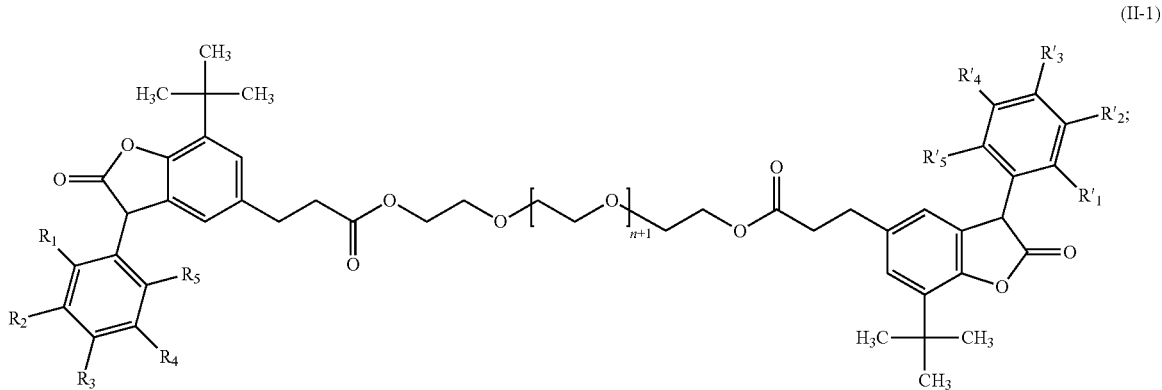

(II-1)

wherein n is an integer from 1 to 24, $R_1$ to $R_5$ and $R'_1$ to $R'_5$ are defined as described at the embodiment of the compound of formula (I-1).

The preferences and combination of preferences for n, $R_1$ to $R_5$, $R'_1$ to $R'_5$ and E, which are described at the embodiment of the compound of the formula (I-1), apply similarly to the stabilizer mixture [I-1-II-2].

Preferred is a stabilizer mixture [I-1-II-1], wherein the weight ratio between the compound of the formula (I-1) and the compound of the formula (II-1) is from 0.1 to 10.

Preferred is a stabilizer mixture [I-1-II-1], which comprises b-I-1) a compound of formula (I-1);
b-I-2) a compound of formula (I-2);
b-I-3) a compound of formula (I-3);
b-II-1) a compound of formula (II-1);
b-II-2) a compound of formula (II-2)

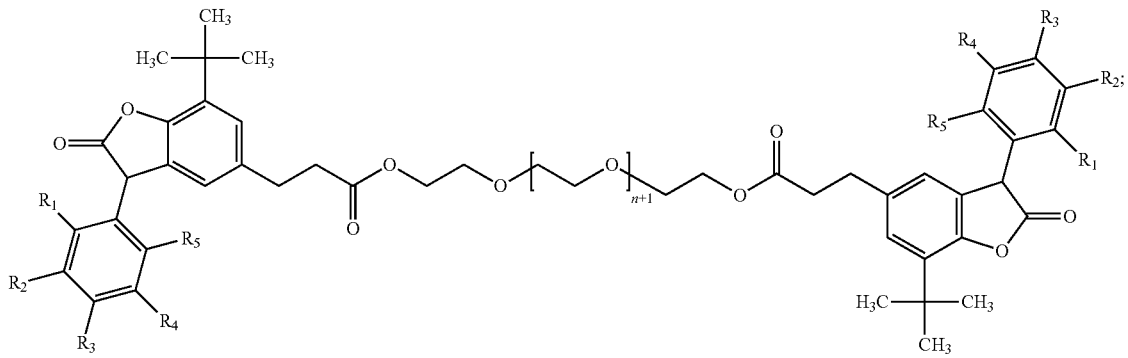

(II-2)

and b-II-3) a compound of formula (II-3)

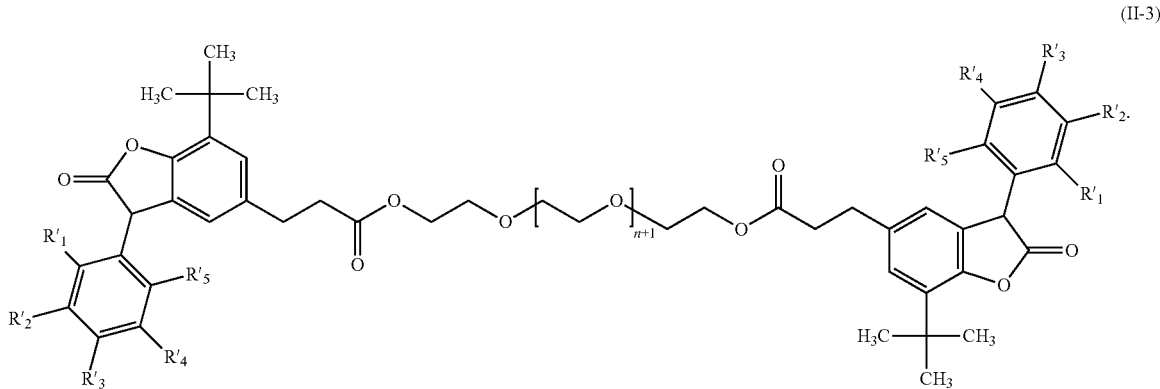

Preferred is a stabilizer mixture [I-1-II-1], which comprises
- b-I-1) a compound of the formula (I-1);
- b-I-2) a compound of the formula (I-2);
- b-I-3) a compound of the formula (I-3);
- b-II-1) a compound of the formula (II-1);
- b-II-2) a compound of the formula (II-2); and
- b-II-3) a compound of the formula (II-3);

wherein $R_1$ is different to $R'_1$, $R_2$ is different to $R'_2$, $R_3$ is different to $R'_3$, $R_4$ is different to $R'_4$, or $R_5$ is different to $R'_5$, the weight ratio between the compound of the formula (I-1) and the compound of the formula (II-1) is from 0.1 to 10, the weight ratio between the compound of the formula (I-1) and the compound of the formula (I-2) is from 0.1 to 10, the weight ratio between the compound of the formula (I-1) and the compound of the formula (I-3) is from 0.01 to 100, the weight ratio between the compound of the formula (II-1) and the compound of the formula (II-2) is from 0.1 to 10, and the weight ratio between the compound of the formula (II-1) and the compound of the formula (II-3) is from 0.01 to 100.

Preferred is a stabilizer mixture [I-1-II-1], which comprises
- b-I-1) a compound of the formula (I-1);
- b-II-1) a compound of the formula (II-1); and
- b-X-1) a compound of the formula (X-1)

Preferred is a stabilizer mixture [I-1-II-1], which comprises

- b-I-1) a compound of the formula (I-1);

- b-II-1) a compound of the formula (II-1); and

- b-X-1) a compound of the formula (X-1);

wherein n is an integer from 1 to 23, the weight ratio between the compound of the formula (I-1) and the compound of the formula (II-1) is from 0.1 to 10, and the weight ratio between the compound of the formula (I-1) and the compound of the formula (X-1) is from 0.1 to 10.

Preferred is a stabilizer mixture [I-1-II-1], which comprises

- b-I-1) a compound of the formula (I-1);

- b-II-1) a compound of the formula (II-1);

- b-X-1) a compound of the formula (X-1); and

- b-XI-1) a compound of the formula (XI-1)

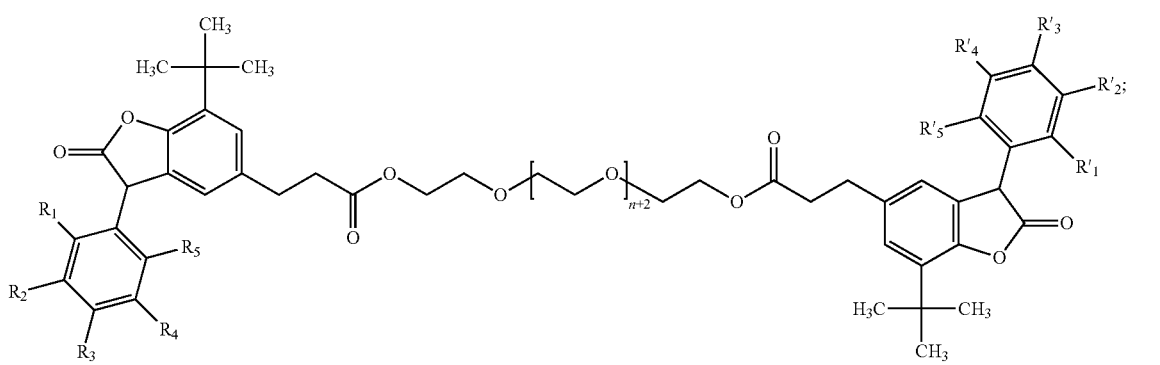

wherein n is an integer from 1 to 23.

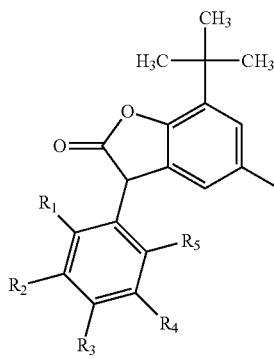

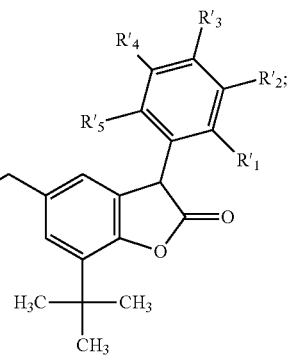

wherein n is an integer from 1 to 22.

Preferred is a stabilizer mixture [I-1-II-1], which comprises
- b-I-1) a compound of the formula (I-1);
- b-II-1) a compound of the formula (II-1);
- b-X-1) a compound of the formula (X-1); and
- b-XI-1) a compound of the formula (XI-1)

wherein n is an integer from 1 to 22, the weight ratio between the compound of the formula (I-1) and the compound of the formula (II-1) is from 0.1 to 10, the weight ratio between the compound of the formula (I-1) and the compound of the formula (X-1) is from 0.1 to 10, and the weight ratio between the compound of the formula (I-1) and the compound of the formula (XI-1) is from 0.1 to 10.

A further embodiment of the invention is a stabilizer mixture [I-1-III-2], which comprises
- b-I-1) a compound of formula (I-1); and
- b-III-2) a compound of formula (III-2)

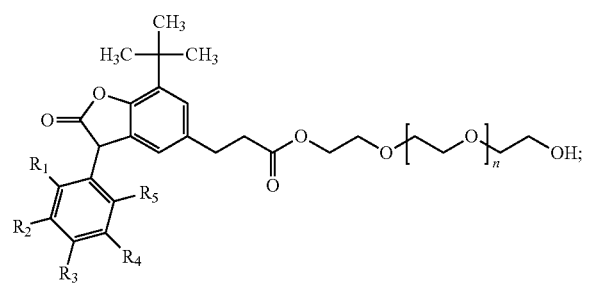

wherein n, $R_1$ to $R_5$ and $R'_1$ to $R'_5$ are defined as described at the embodiment of the compound of formula (I-1).

A compound of formula (III-2) possesses at least one asymmetric carbon atom, i.e. the carbon atom at the 3-position of the benzofuran-2-one ring, which results in enantiomers. The invention relates to any one of these enantiomers or mixtures thereof. Several combinations of substituents at formula (III-2) lead to the presence of at least two asymmetric carbon atoms, which results in diastereomers. The invention relates to any one of these diastereomers or mixtures thereof.

The preferences and combination of preferences for n, $R_1$ to $R_5$, $R'_1$ to $R'_5$ and E, which are described at the embodiment of the compound of formula (I-1), apply similarly to the stabilizer mixture [I-1-III-2].

Preferred is a stabilizer mixture [I-1-III-2], wherein the weight ratio between a compound of the formula (I-1) and a compound of the formula (III-2) is from 0.2 to 40, in particular from 1 to 40 and especially from 5 to 40.

Preferred is a stabilizer mixture [I-1-III-2], which comprises
- b-I-1) a compound of the formula (I-1);
- b-III-2) a compound of the formula (III-2); and
- b-III-3) a compound of the formula (III-3)

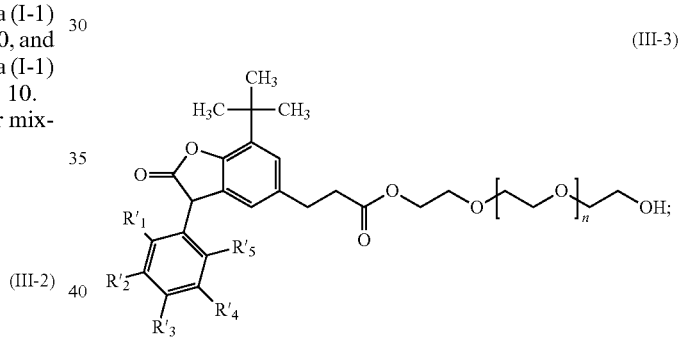

wherein $R_1$ is different to $R'_1$, $R_2$ is different to $R'_2$, $R_3$ is different to $R'_3$, $R_4$ is different to $R'_4$, or $R_5$ is different to $R'_5$.

A compound of formula (III-3) possesses at least one asymmetric carbon atom, i.e. the carbon atom at the 3-position of the benzofuran-2-one ring, which results in enantiomers. The invention relates to any one of these enantiomers or mixtures thereof. Several combinations of substituents at formula (III-3) lead to the presence of at least two asymmetric carbon atoms, which results in diastereomers. The invention relates to any one of these diastereomers or mixtures thereof.

Preferred is a stabilizer mixture [I-1-III-2], which comprises
- b-I-1) a compound of the formula (I-1);
- b-III-2) a compound of the formula (III-2); and
- b-III-3) a compound of the formula (III-3);

wherein $R_1$ is different to $R'_1$, $R_2$ is different to $R'_2$, $R_3$ is different to $R'_3$, $R_4$ is different to $R'_4$, or $R_5$ is different to $R'_5$, the weight ratio between a compound of the formula (I-1) and a compound of the formula (III-2) is from 0.2 to 40, in particular from 1 to 40 and especially from 5 to 40, and the weight ratio between a compound of the formula (I-1) and a compound of the formula (III-2) is from 0.2 to 40, in particular from 1 to 40 and especially from 5 to 40.

Preferred is a stabilizer mixture [I-1-III-2], which comprises
- b-I-1) a compound of the formula (I-1);
- b-I-2) a compound of the formula (I-2);
- b-I-3) a compound of the formula (I-3);
- b-III-2) a compound of the formula (III-2); and
- b-III-3) a compound of the formula (III-3)

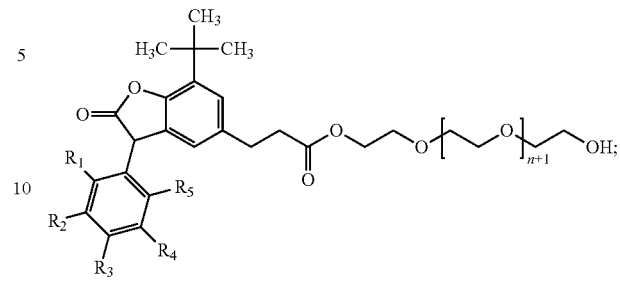

(III-3)

wherein $R_1$ is different to $R'_1$, $R_2$ is different to $R'_2$, $R_3$ is different to $R'_3$, $R_4$ is different to $R'_4$, or $R_5$ is different to $R'_5$.

Preferred is a stabilizer mixture [I-1-III-2], which comprises
- b-I-1) a compound of the formula (I-1);
- b-I-2) a compound of the formula (I-2);
- b-I-3) a compound of the formula (I-3);
- b-III-2) a compound of the formula (III-2); and
- b-III-3) a compound of the formula (III-3);

wherein $R_1$ is different to $R'_1$, $R_2$ is different to $R'_2$, $R_3$ is different to $R'_3$, $R_4$ is different to $R'_4$, or $R_5$ is different to $R'_5$, the weight ratio between the compound of the formula (I-1) and the compound of the formula (I-2) is from 0.1 to 10, the weight ratio between the compound of the formula (I-1) and the compound of the formula (I-3) is from 0.01 to 100, the weight ratio between a compound of the formula (I-1) and a compound of the formula (III-2) is from 0.2 to 40, in particular from 1 to 40 and especially from 5 to 40, and the weight ratio between a compound of the formula (I-1) and a compound of the formula (III-3) is from 0.2 to 40, in particular from 1 to 40 and especially from 5 to 40.

Preferred is a stabilizer mixture [I-1-III-2], which comprises
- b-I-1) a compound of formula (I-1);
- b-II-1) a compound of formula (II-1);
- b-III-2) a compound of formula (III-2); and
- b-IV-2) a compound of formula (IV-2)

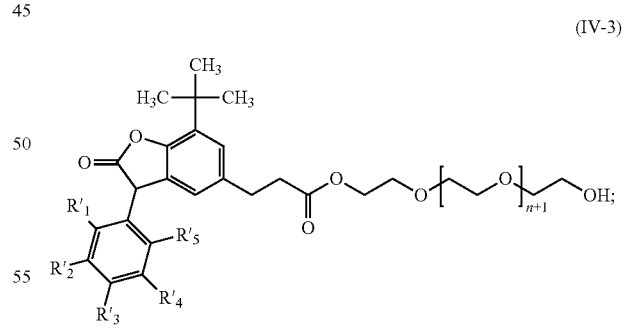

(IV-2)

wherein n is an integer from 1 to 24.

Preferred is a stabilizer mixture [I-1-III-2], which comprises
- b-I-1) a compound of formula (I-1);
- b-II-1) a compound of formula (II-1);
- b-III-2) a compound of formula (III-2); and
- b-IV-2) a compound of formula (IV-2);

wherein n is an integer from 1 to 24, the weight ratio between the compound of the formula (I-1) and the compound of the formula (II-1) is from 0.1 to 10, the weight ratio between the compound of the formula (I-1) and the compound of the formula (III-2) is from 0.2 to 40, in particular from 1 to 40 and especially from 5 to 40, and the weight ratio between the compound of the formula (II-2) and the compound of the formula (IV-2) is from 0.2 to 40, in particular from 1 to 40 and especially from 5 to 40.

Preferred is a stabilizer mixture [I-1-III-2], which comprises
- b-I-1) a compound of the formula (I-1);
- b-I-2) a compound of the formula (I-2);
- b-I-3) a compound of the formula (I-3);
- b-II-1) a compound of the formula (II-1);
- b-II-2) a compound of the formula (II-2);
- b-II-2) a compound of the formula (II-3);
- b-III-2) a compound of the formula (III-2);
- b-III-3) a compound of the formula (III-3);
- b-IV-2) a compound of the formula (IV-2); and
- b-IV-3) a compound of the formula (IV-3)

(IV-3)

wherein n is an integer from 1 to 24, and $R_1$ is different to $R'_1$, $R_2$ is different to $R'_2$, $R_3$ is different to $R'_3$, $R_4$ is different to $R'_4$, or $R_5$ is different to $R'_5$.

Preferred is a stabilizer mixture [I-1-III-2], which comprises
- b-I-1) a compound of the formula (I-1);
- b-I-2) a compound of the formula (I-2);
- b-I-3) a compound of the formula (I-3);
- b-II-1) a compound of the formula (II-1);

b-II-2) a compound of the formula (II-2);
b-II-2) a compound of the formula (II-3);
b-III-2) a compound of the formula (III-2);
b-III-3) a compound of the formula (III-3);
b-IV-2) a compound of the formula (IV-2); and
b-IV-3) a compound of the formula (IV-3);
wherein n is an integer from 1 to 24,
$R_1$ is different to $R'_1$, $R_2$ is different to $R'_2$, $R_3$ is different to $R'_3$, $R_4$ is different to $R'_4$, or $R_5$ is different to $R'_5$,
the weight ratio between the compound of the formula (I-1) and the compound of the formula (I-2) is from 0.1 to 10,
the weight ratio between the compound of the formula (I-1) and the compound of the formula (I-3) is from 0.01 to 100,
the weight ratio between a compound of the formula (I-1) and the compound of the formula (III-2) is from 0.2 to 40, in particular from 1 to 40 and especially from 5 to 40,
the weight ratio between the compound of the of the formula (I-1) and the compound of the formula (III-3) is from 0.2 to 40, in particular from 1 to 40 and especially from 5 to 40,
the weight ratio between the compound of the formula (I-1) and the compound of the formula (II-1) is from 0.1 to 10,
the weight ratio between the compound of the formula (II-1) and the compound of the formula (II-2) is from 0.1 to 10,
the weight ratio between the compound of the formula (II-1) and the compound of the formula (II-3) is from 0.01 to 100,
the weight ratio between the compound of the formula (II-1) and the compound of the formula (IV-2) is from 0.2 to 40, in particular from 1 to 40 and especially from 5 to 40, and
the weight ratio between the compound of the formula (II-1) and the compound of formula (IV-3) is from 0.2 to 40, in particular from 1 to 40 and especially from 5 to 40.

Preferred is a stabilizer mixture [I-1-III-2], which comprises
b-I-1) a compound of the formula (I-1);
b-II-1) a compound of the formula (II-1);
b-III-2) a compound of the formula (III-2);
b-IV-2) a compound of the formula (IV-2); and
b-X-1) a compound of the formula (X-1);
wherein n is an integer from 1 to 23.

Preferred is a stabilizer mixture [I-1-III-2], which comprises
b-I-1) a compound of the formula (I-1);
b-II-1) a compound of the formula (II-1);
b-II-2) a compound of the formula (III-2);
b-IV-2) a compound of the formula (IV-2); and
b-X-1) a compound of the formula (X-1);
wherein n is an integer from 1 to 23,
the weight ratio between the compound of the formula (I-1) and the compound of the formula (II-1) is from 0.1 to 10,
the weight ratio between the compound of the formula (I-1) and the compound of the formula (III-2) is from 0.2 to 40, in particular from 1 to 40 and especially from 5 to 40,
the weight ratio between the compound of the formula (II-2) and the compound of the formula (IV-2) is from 0.2 to 40, in particular from 1 to 40 and especially from 5 to 40, and
the weight ratio between the compound of the formula (I-1) and the compound of the formula (X-1) is from 0.1 to 10.

Preferred is a stabilizer mixture [I-1-III-2], which comprises
b-I-1) a compound of the formula (I-1);
b-II-1) a compound of the formula (II-1);
b-III-2) a compound of the formula (III-2);
b-IV-2) a compound of the formula (IV-2);
b-X-1) a compound of the formula (X-1); and
b-XI-1) a compound of the formula (XI-1);
wherein n is an integer from 1 to 22.

Preferred is a stabilizer mixture [I-1-III-2], which comprises
b-I-1) a compound of the formula (I-1);
b-II-1) a compound of the formula (II-1);
b-III-2) a compound of the formula (III-2);
b-IV-2) a compound of the formula (IV-2);
b-X-1) a compound of the formula (X-1); and
b-XI-1) a compound of the formula (XI-1);
wherein n is an integer from 1 to 22,
the weight ratio between the compound of the formula (I-1) and the compound of the formula (II-1) is from 0.1 to 10,
the weight ratio between the compound of the formula (I-1) and the compound of the formula (III-2) is from 0.2 to 40, in particular from 1 to 40 and especially from 5 to 40,
the weight ratio between the compound of the formula (II-2) and the compound of the formula (IV-2) is from 0.2 to 40, in particular from 1 to 40 and especially from 5 to 40,
the weight ratio between the compound of the formula (I-1) and the compound of the formula (X-1) is from 0.1 to 10, and
the weight ratio between the compound of the formula (I-1) and the compound of the formula (XI-1) is from 0.1 to 10.

A further embodiment of the invention is a product [P-V-2/3] obtainable by reacting a compound of the formula (V-2)

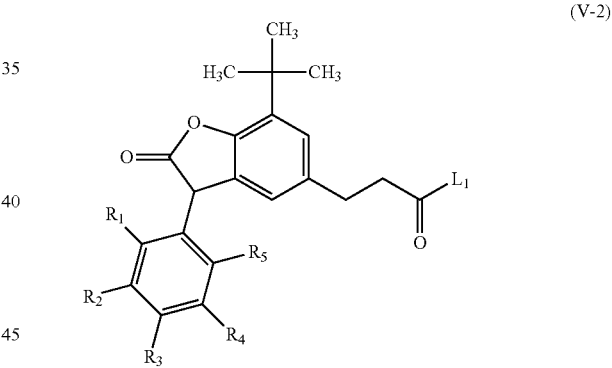

(V-2)

and a compound of the formula (V-3)

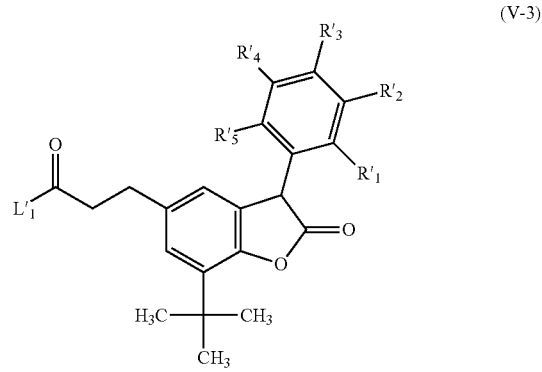

(V-3)

with a mixture of diols, which comprise
m-VI) a compound of the formula (VI)

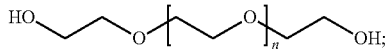

and
m-VII) a compound of the formula (VII)

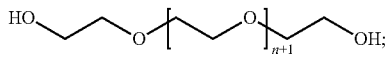

characterized in that the product contains
b-I-1) a compound of the formula (I-1); and
b-II-1) a compound of the formula (II-1);
wherein
n is an integer from 1 to 24,
$R_1$ to $R_5$ and $R'_1$ to $R'_5$ are defined as described at the embodiment of the compound of formula (I-1); and
$L_1$ and $L'_1$ are each independently from each other hydroxy or $C_1$-$C_6$-alkyl-oxy.

Preferably, the reacting takes place at a temperature between 5 and 200° C.

Preferably, the reacting takes place in the presence of a solvent, in particular in a solvent, which does not contain hydroxy groups.

Preferably, the reacting takes place in the presence of a catalyst, in particular an acidic catalyst and especially a solid acidic catalyst.

Preferably, the by-products $L_1$-H and $L'_1$-H are removed during reacting, in particular by application of a vacuum and/or distillation. Especially preferred is the co-distillation, in particular under vacuum, with a solvent, which is preferably returned to the reacting after separation from $L_1$-H and $L'_1$-H.

Preferably, the molar ratio between the summarized molar amounts of the compounds of the formulae (V-2) or (V-3) and the summarized molar amounts of the diols is from 1 to 3, especially 1.5 to 2.5 and in particular 1.8 to 2.2.

The preferences and combination of preferences for n, $R_1$ to $R_5$, $R'_1$ to $R'_5$ and E, which are described at the embodiment of the compound of formula (I-1), apply similarly to the product [P-V-2/3].

Preferred is a product [P-V-2/3], wherein
the weight ratio between a compound of the formula (I-1) and a compound of the formula (II-1) is from 0.1 to 10.

Preferred is a product [P-V-2/3], wherein the product contains
b-I-1) a compound of the formula (I-1);
b-II-1) a compound of the formula (II-1);
b-III-2) a compound of the formula (III-2); and
b-IV-2) a compound of the formula (IV-2).

Preferred is a product [P-V-2/3], wherein the product contains
b-I-1) a compound of the formula (I-1);
b-II-1) a compound of the formula (II-1);
b-III-1) a compound of the formula (III-2); and
b-IV-1) a compound of the formula (IV-2);
wherein the weight ratio between the compound of the formula (I-1) and the compound of the formula (II-1) is from 0.1 to 10, the weight ratio between the compound of the formula (I-1) and the compound of the formula (III-2) is from 0.2 to 40, in particular from 1 to 40 and especially from 5 to 40, and the weight ratio between a compound of the formula (II-2) and a compound of the formula (IV-2) is from 0.2 to 40, in particular from 1 to 40 and especially from 5 to 40.

Preferred is a product [P-V-2/3], wherein the product contains
b-I-1) a compound of the formula (I-1);
b-I-2) a compound of the formula (I-2);
b-I-3) a compound of the formula (I-3);
b-II-1) a compound of the formula (II-1);
b-II-2) a compound of the formula (II-2);
b-II-2) a compound of the formula (II-3);
b-III-2) a compound of the formula (III-2);
b-III-3) a compound of the formula (III-3);
b-IV-2) a compound of the formula (IV-2);
b-IV-3) a compound of the formula (IV-3); and
$R_1$ is different to $R'_1$, $R_2$ is different to $R'_2$, $R_3$ is different to $R'_3$, $R_4$ is different to $R'_4$, or $R_5$ is different to $R'_5$.

Preferred is a product [P-V-2/3], wherein the product contains
b-I-1) a compound of the formula (I-1);
b-I-2) a compound of the formula (I-2);
b-I-3) a compound of the formula (I-3);
b-II-1) a compound of the formula (II-1);
b-II-2) a compound of the formula (II-2);
b-II-2) a compound of the formula (II-3);
b-III-2) a compound of the formula (III-2);
b-III-3) a compound of the formula (III-3);
b-IV-2) a compound of the formula (IV-2); and
b-IV-3) a compound of the formula (IV-3);
wherein $R_1$ is different to $R'_1$, $R_2$ is different to $R'_2$, $R_3$ is different to $R'_3$, $R_4$ is different to $R'_4$, or $R_5$ is different to $R'_5$, the weight ratio between the compound of the formula (I-1) and the compound of the formula (I-2) is from 0.1 to 10, the weight ratio between the compound of the formula (I-1) and the compound of the formula (I-3) is from 0.01 to 100, the weight ratio between a compound of the formula (I-1) and a compound of the formula (III-2) is from 0.2 to 40, in particular from 1 to 40 and especially from 5 to 40, the weight ratio between a compound of the of the formula (I-1) and a compound of the formula (III-3) is from 0.2 to 40, in particular from 1 to 40 and especially from 5 to 40, the weight ratio between the compound of the formula (I-1) and the compound of the formula (II-1) is from 0.1 to 10, the weight ratio between the compound of the formula (II-1) and the compound of the formula (II-2) is from 0.1 to 10, the weight ratio between the compound of the formula (II-1) and the compound of the formula (II-3) is from 0.01 to 100, the weight ratio between the compound of the formula (II-1) and the compound of the formula (IV-2) is from 0.2 to 40, in particular from 1 to 40 and especially from 5 to 40, and the weight ratio between the compound of formula (II-1) and the compound of the formula (IV-3) is from 0.2 to 40, in particular from 1 to 40 and especially from 5 to 40.

Preferred is a product [P-V-2/3] obtainable by reacting a compound of the formula (V-2) and a compound of the formula (V-3) with a mixture of diols, which comprises m-VI) a compound of the formula (VI);
m-VII) a compound of the formula (VII); and
m-VIII) a compound of the formula (VIII)

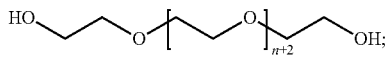
(VIII)

characterized in that the product contains
b-I-1) a compound of the formula (I-1);
b-II-1) a compound of the formula (II-1);
b-X-1) a compound of the formula (X-1); and
wherein n is an integer from 1 to 23.

Preferred is a product [P-V-2/3] obtainable by reacting a compound of the formula (V-2) and a compound of the formula (V-3) with a mixture of diols, which comprises
m-VI) a compound of the formula (VI);
m-VII) a compound of the formula (VII); and
m-VIII) a compound of the formula (VIII);
characterized in that the product contains
b-I-1) a compound of the formula (I-1);
b-II-1) a compound of the formula (II-1);
b-X-1) a compound of the formula (X-1);
wherein n is an integer from 1 to 23,
the weight ratio between the compound of the formula (I-1) and the compound of the formula (II-1) is from 0.1 to 10, and
the weight ratio between the compound of the formula (I-1) and the compound of the formula (X-1) is from 0.1 to 10.

Preferred is a product [P-V-2/3] obtainable by reacting a compound of the formula (V-2) and a compound of the formula (V-3) with a mixture of diols, which comprises
m-VI) a compound of the formula (VI);
m-VII) a compound of the formula (VII);
m-VIII) a compound of the formula (VIII); and
m-IX) a compound of the formula (IX)

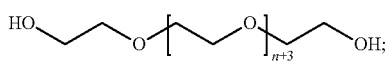
(IX)

characterized in that the product contains
b-I-1) a compound of the formula (I-1);
b-II-1) a compound of the formula (II-1);
b-X-1) a compound of the formula (X-1);
b-XI-1) a compound of the formula (XI-1); and
wherein n is an integer from 1 to 22.

Preferred is a product [P-V-2/3] obtainable by reacting a compound of the formula (V-2) and a compound of the formula (V-3) with a mixture of diols, which comprises
m-VI) a compound of the formula (VI);
m-VII) a compound of the formula (VII);
m-VIII) a compound of the formula (VIII); and
m-IX) a compound of the formula (IX);
characterized in that the product contains
b-I-1) a compound of the formula (I-1);
b-II-1) a compound of the formula (II-1);
b-X-1) a compound of the formula (X-1);
b-XI-1) a compound of the formula (XI-1);
wherein n is an integer from 1 to 22,
the weight ratio between the compound of the formula (I-1) and the compound of the formula (II-1) is from 0.1 to 10,
the weight ratio between the compound of the formula (I-1) and the compound of the formula (X-1) is from 0.1 to 10, and
the weight ratio between the compound of the formula (I-1) and the compound of the formula (XI-1) is from 0.1 to 10.

Polyethylene glycol is a class of diols, which can be either a single compound of or consists essentially of a mixture of compounds of the following formula:

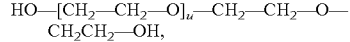

wherein u is an integer from 2 to 25. Polyethylene glycols are known and partly commercially available. Examples of polyethylene glycol are: PEG 200 (an average molecular weight of about 190-210), PEG 300 (an average molecular weight of about 285-315), PEG 400 (an average molecular weight of about 380-420), PEG 600 (an average molecular weight of about 570-613) or PEG 900 (an average molecular weight of about 855-900).

Preferred is a product [P-V-2/3], wherein the mixture of diols consists essentially of polyethylene glycols of the summary formula

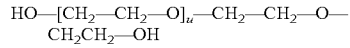

wherein u is an integer from 2 to 25, especially from 1 to 9 and in particular from 1 to 8.

A further embodiment of the present invention is a composition, which comprises
a) an organic material susceptible to oxidative, thermal or light-induced degradation; and
b) a compound of the formula (I-1) as defined above.

Preferred is a composition, which comprises
a) an organic material susceptible to oxidative, thermal or light-induced degradation; and
b) a stabilizer mixture [I-1/2/3] as defined above, a stabilizer mixture [I-1-II-1] as defined above, a stabilizer mixture [I-1-III-2] as defined above or a product [P-V-2/3] as defined above.

Preferred is a composition, which comprises
a) an organic material susceptible to oxidative, thermal or light-induced degradation; and
b) a stabilizer mixture [I-1-II-1] as defined above.

Preferred is a composition, which comprises
a) an organic material susceptible to oxidative, thermal or light-induced degradation; and
b) a stabilizer mixture [I-1-III-2] as defined above.

Preferred is a composition, which comprises
a) an organic material susceptible to oxidative, thermal or light-induced degradation; and
b) a product [P-V-2/3] as defined above.

The organic material of the present invention is susceptible to oxidative, thermal or light-induced degradation. Preferably, the organic material is a polymer, a wax, a mineral oil or a fat, especially a polymer.

Preferred is a composition, wherein component a) is a polymer.

Examples of a polymer are:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be cross-linked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is generated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

A special copolymer of two monoolefins is a pipe grade polypropylene random copolymer, which is obtainable from the polymerization of more than 90% by weight of propylene and of less than 10% by weight, typically between 2 and 6% by weight, of ethylene.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyl-toluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylenelstyrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes, for example polyurethanes synthesized from a polyol and an aliphatic or aromatic polyisocyanate such as polyurethanes derived from hydroxyl-terminated polyethers, polyesters or polybutadienes on the one hand and aliphatic or aromatic polyisocyanates on the other, as well as precursors thereof.

Hydroxyl-terminated polyethers are known and are prepared, for example, by polymerizing epoxides such as ethylene oxide, propylene oxide, butylene oxide, tetrahydrofuran, styrene oxide or epichlorohydrin with themselves, for example in the presence of $BF_3$, or by addition reaction of these epoxides, alone or as a mixture or in succession, with starting components containing reactive hydrogen atoms, such as water, alcohols, ammonia or amines, for example ethylene glycol, propylene 1,3- and 1,2-glycol, trimethylolpropane, 4,4'-dihydroxydiphenylpropane, aniline, ethanolamine or ethylenediamine. Sucrose polyethers are also suitable in accordance with the invention. In many cases preference is given to those polyethers which predominantly (up to 90% by weight, based on all the OH groups present in the polyether) contain primary OH groups. Furthermore, polyethers modified by vinyl polymers, as are formed, for example, by polymerizing styrene and acrylonitrile in the presence of polyethers, are suitable, as are polybutadienes containing OH groups.

In particular, a polyol compound has a molecular weight of 400-10000, especially 800 to 10000, and is a polyhydroxy compound, especially containing from 2 to 8 hydroxyl groups, especially from 2 to 4.

Suitable polyisocyanates are aliphatic or aromatic, for example ethylene diisocyanate, 1,4-tetramethylene diisocyanate, 1,6-hexamethylene diisocyanate, 1,12-dodecane diisocyanate, cyclobutane 1,3-diisocyanate, cyclohexane 1,3- and -1,4-diisocyanate and also any desired mixtures of these isomers, 1-isocyanato-3,3,5-trimethyl-5-isocyanatomethylcyclohexane, 2,4- and 2,6-hexahydrotolylene diisocyanate and also any desired mixtures of these isomers, hexahydro-1,3- and/or -1,4-phenylene diisocyanate, perhydro-2,4'- and/or -4,4'-diphenylmethanediisocyanate, 1,3- and 1,4-phenylene diisocyanate, 2,4- and 2,6-tolylene diisocyanate, and also any desired mixtures of these isomers, diphenylmethane 2,4'- and/or -4,4'-diisocyanate, naphthylene 1,5-diisocyanate, triphenylmethane 4,4',4''-triisocyanate, polyphenyl-polymethylene polyisocyanates as are obtained by aniline-formaldehyde condensation followed by phosgenization, m- and p-isocyanatophenylsulfonyl isocyanates, perchlorinated aryl polyisocyanates, polyisocyanates containing carbodiimide groups, polyisocyanates containing allophanate groups, polyisocyanates containing isocyanurate groups, polyisocyanates containing urethane groups, polyisocyanates containing acylated urea groups, polyisocyanates containing biuret groups, polyisocyanates containing ester groups, reaction products of the abovementioned isocyanates with acetals, and polyisocyanates containing polymeric fatty acid radicals.

It is also possible to employ the isocyanate group-containing distillation residues, as they are or dissolved in one or more of the abovementioned polyisocyanates, which are obtained in the course of the industrial preparation of isocyanates. It is additionally possible to use any desired mixtures of the abovementioned polyisocyanates.

Preferred are 2,4- or 2,6-tolylene diisocyanate and any desired mixtures of these isomers ("TDI"), polyphenyl-polymethylene-polyisocyanates as prepared by aniline-formaldehyde condensation followed by phosgenization ("crude MDI") or polyisocyanates containing carbodiimide, urethane, allophanate, isocyanurate, urea or biuret groups ("modified polyisocyanates").

The polyurethanes can be homogeneous polyurethanes or cellular.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimides, polyesterimides, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylenesuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homopolymer of preferably poly-L-lactide and any of its blends or alloys with other polymers; a co-polymer of lactic acid or lactide with other monomers, such as hydroxy-carboxylic acids, like for example glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.
20. Polyketones.
21. Polysulfones, polyether sulfones and polyether ketones.
22. Cross-linked polymers derived from aldehydes on the one hand and phenols, ureas and melamines on the other hand, such as phenol/formaldehyde resins, urea/formal-dehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Cross-linkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Cross-linked epoxy resins derived from aliphatic, cycloaliphatic, heterocyclic or aromatic glycidyl compounds, e.g. products of diglycidyl ethers of bisphenol A and bisphenol F, which are cross-linked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or latices of carboxylated styrene/butadiene copolymers.

A polymer can be natural, semi-synthetic or synthetic. A natural polymer is isolated from a natural source without further synthetic modifications. A synthetic polymer does not contain a polymer part isolated from a natural source. A semi-synthetic polymer contains at least one natural polymer part, wherein the natural polymer part can be synthetically modified and/or reacted with monomers to form the semi-synthetic polymer.

A polymer can be thermoplastic, i.e. it can be shaped into a new form at an elevated temperature, for example at a temperature in the range from 150° C. to 340° C.

Preferred is a composition, wherein component a) is a semi-synthetic or synthetic polymer.

Preferred is a composition, wherein component a) is a thermoplastic polymer.

Preferred is a composition, wherein component a) is a polymer, which is synthetic and thermoplastic.

Preferred is a composition, wherein component a) is a polyolefin, a polyether polyol or a polyurethane.

The employed amount of component b) in regard to component a) varies with the particular organic material and the desired degree of protection. The content of component b) refers herein to the amount of a compound of the formula (I-1) or, if other compounds of the formulae (I-2), (I-3), (II-1), (II-2), (II-3), (III-2), (III-3), (IV-2), (IV-3), (X-1) or (XI-1) are present, to the summarized amount of compounds of the aforementioned formulae. This applies especially in case that component b) is a stabilizer mixture [I-1/2/3] as defined above, a stabilizer mixture [I-1-II-1] as defined above, a stabilizer mixture [I-1-III-2] as defined above or a product [P-V-2/3] as defined above.

Preferred is a composition, which comprises a component a) and a component b), wherein component b) is contained in an amount of 0.0001% to 10%, in particular from 0.0005 to 2%, very particular from 0.001 to 2% and especially from 0.005 to 1%, based on the weight of component a).

Optionally, a composition comprising a component a) and a component b) contains as component c) a further additive.

A further additive can be selected from the following list:
1. Antioxidants
  1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol, 2,4-dimethyl-6-(1'-methyl-1'-tetradecyl-methyl)-phenol and mixtures thereof.
  1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.
  1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.
  1.4. Tocopherols, for example α-tocopherol, β-tocopherol, γ-tocopherol, δ-tocopherol and mixtures thereof (vitamin E).
  1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'- thiobis(6-tert-butyl-2-methylphenol), 4,4'-thiobis(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methyl benzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)-propane, 2,2-bis-(5-tert-butyl-4-hydroxy-2-methylphenyl)-4-n-dodecylmercaptobutane, 1,1,5,5-tetra(5-tert-butyl-4-hydroxy-2-methylphenyl)pentane.

1.7. O-, N- and S-benzyl compounds, for example 3,5,3',5'-tetra-tert-butyl-4,4'-di-hydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzyl-mercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methyl-benzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of 3-(3,5-di-tert-butyl-4-hydroxyphenyl)propionic acid with mono- or polyhydric alcohols, for example with methanol, ethanol, n-octanol, i-octanol, octadecanol, a mixture of linear and branched $C_{13}$-$C_{15}$-alkanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxylethyl)isocyanurate, N,N'-bis-(hydroxylethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of 3-(5-tert-butyl-4-hydroxy-3-methylphenyl) propionic acid with mono- or polyhydric alcohols, for example with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxa bicyclo[2.2.2]octane; 3,9-bis[2-{3-(3-tert-butyl-4-hydroxy-5-methyl-phenyl)propionyloxy}-1,1-dimethylethyl]-2,4,8,10-tetraoxaspiro[5.5]undecane.

1.15. Esters of 3-(3,5-dicyclohexyl-4-hydroxyphenyl)propionic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]-octane.

1.16. Esters of 3,5-di-tert-butyl-4-hydroxyphenyl acetic acid with mono- or polyhydric alcohols, for example with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of 3-(3,5-di-tert-butyl-4-hydroxyphenyl)propionic acid, for example N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]-propionyloxy)ethyl]oxamide (Naugard XL-1 ®, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)-phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV absorbers and light stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxy-phenyl)benzotriazole, 2-(2'-hydroxy-4'-octyloxyphenyl)benzotriazole, 2-(3',5'-di-tertamyl-2'-hydroxyphenyl)benzotriazole, 2-(3',5'-bis(α,α-dimethylbenzyl)-2'-hydroxy-phenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxy-phenyl)-5-chlorobenzotriazole, 2-(3'-tert-butyl-2'-hydroxy-5'-(2-methoxycarbonylethyl)-phenyl)-5-chlorobenzotriazole, 2-(3'-tert-butyl-2'-hydroxy-5'-(2-methoxycarbonylethyl)-phenyl)benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl-2'-hydroxyphenyl)-2H-benzotriazole with polyethylene glycol 300;

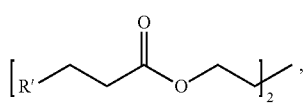

where R'=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline and neopentyl tetra(α-cyano-β,β-diphenylacrylate).

2.5. Nickel compounds, for example nickel complexes of 2,2'-thiobis[4-(1,1,3,3-tetra-methylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)-sebacate, bis(2,2,6,6-tetramethyl-4-piperidyl)succinate, bis(1,2,2,6,6-pentamethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetra-methylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decane-2,4-dione, bis(1-octyloxy-2,2,6,6-tetramethylpiperid-4-yl) sebacate, bis(1-octyloxy-2,2,6,6-tetramethylpiperid-4-yl) succinate, bis-[2,2,6,6-tetramethyl-1-(undecyloxy)-piperidin-4-yl]carbonate, linear or cyclic condensates of N,N'-bis(2,2,6,6-tetramethyl-4-piperidyl)-hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)ethane, the condensate of 2-chloro-4,6-di-(4-n-butylamino-1,2,2,6,6-pentamethylpiperidyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268 64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)-ethene, N,N'-bis-formyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, a mixture of oligomeric compounds which are the formal condensation products of N,N'-bis-(2,2,6,6-tetramethyl-1-propoxy-piperidin-4-yl)-hexane-1,6-diamine and 2,4-dichloro-6-{n-butyl-(2,2,6,6-tetramethyl-1-propoxy-piperidin-4-yl)-amino}-[1,3,5] triazine end-capped with 2-chloro-4,6-bis-(di-n-butylamino)-[1,3,5]triazine, a mixture of oligomeric compounds which are the formal condensation products of N,N'-bis-(2,2,6,6-tetramethyl-piperidin-4-yl)-hexane-1,6-diamine and 2,4-dichloro-6-{n-butyl-(2,2,6,6-tetramethyl-piperidin-4-yl)-amino}-[1,3,5]triazine end-capped with 2-chloro-4,6-bis-(di-n-butylamino)-[1,3,5]triazine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)-oxymethyl-3,3,5-trimethyl-2-morpholinone, the reaction product of 2,4-bis-[(1-cyclo-hexyloxy-2,2,6,6-piperidine-4-yl)butylamino]-6-chloro-s-triazine with N,N'-bis-(3-amino-propyl) ethylenediamine), 1,3,5-tris(N-cyclohexyl-N-(2,2,6,6-tetramethyl-piperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyl¬oxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethyl-phenyl)-1,3,5-triazine, 2-(2-hydroxy-4-hexyloxy)phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]-phenyl}-4,6-bis¬(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenyl-propionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)-thiopropionyl dihydrazide.

4. Phosphites and phosphonites, for example triphenyl phosphite, diphenylalkyl phosphites, phenyldialkyl phosphites, tris(nonylphenyl)phosphite, trilauryl phosphite, trioctadecyl phosphite, distearylpentaerythritol diphosphite, tris(2,4-di-tert-butylphenyl)phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo-[triethyltris(3,3',5,5'-tetra-tert-butyl-1,1'-biphenyl-2,2'-diyl) phosphite], 2-ethylhexyl-(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl)phosphite (Irgafos 168, RTM BASF), tris(nonylphenyl)phosphite,

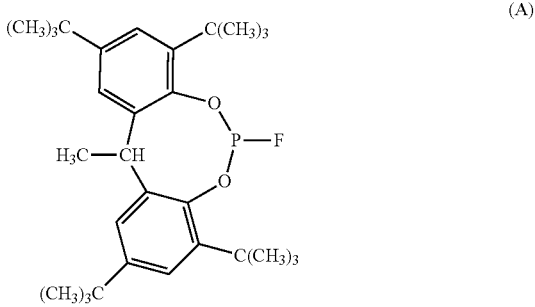

(A)

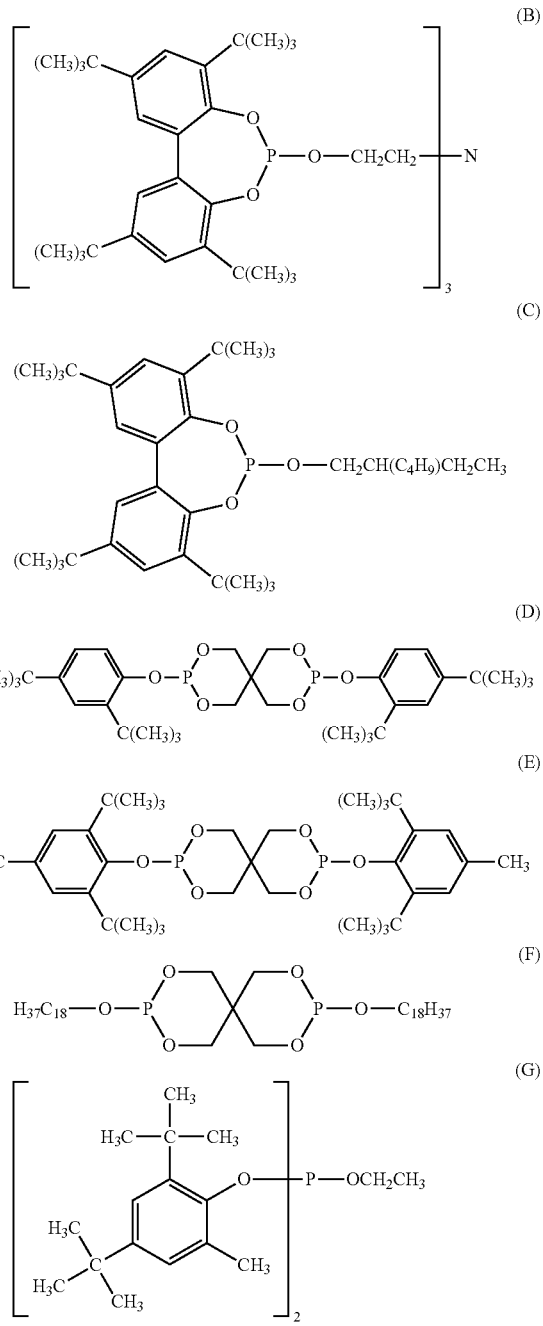

5. Hydroxylamines and amine N-oxides, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine or N,N-bis-(hydrogenated rape-oil alkyl)-N-methyl-amine N-oxide.

6. Nitrones, for example N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-heptadecylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate and pentaerythritol tetrakis-[3-(n-lauryl)-propionic acid ester].

8. Peroxide scavengers, for example esters of α-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese.

10. Acid scavengers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate and zinc pyrocatecholate.

11. Benzofuranones, which are different to compounds of the formulae (I-1), (I-2), (I-3), (II-1), (II-2), (II-3), (III-2), (III-3), (IV-2), (IV-3), (X-1) or (XI-1), and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)-benzofuran-2-one, 3-(4-acetoxy-3,5-di methylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethyl-phenyl)-5,7-di-tert-butylbenzofuran-2-one, 3-(2,3-dimethylphenyl)-5,7-di-tert-butylbenzofuran-2-one and 3-(2-acetoxy-4-(1,1,3,3-tetramethylbutyl)-phenyl)-5-(1,1,3,3-tetramethyl-butyl)-benzofuran-2-one.

12. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers), Irgaclear XT 386 (RTM BASF), 1,3:2,4-bis(3',4'-dimethylbenzylidene)-sorbitol, 1,3:2,4-di(paramethyldibenzylidene)-sorbitol, and 1,3:2,4-di(benzylidene)sorbitol.

13. Fillers and reinforcing agents, for example calcium carbonate, silicates, glass fibres, glass beads, asbestos, talc, kaolin, bentonite, mica, hydrotalcite, barium sulfate, metal oxides and hydroxides, carbon black, graphite, wood flour and flours or fibers of other natural products, synthetic fibers.

14. Flame retardants 14.1 Phosphorus containing flame retardants, reactive phosphorous containing flame retardants, for example tetraphenyl resorcinol diphosphite (Fyrolflex RDP, RTM, Akzo Nobel), tetrakis(hydroxymethyl)phosphonium sulphide, triphenyl phosphate, diethyl-N,N-bis(2-hydroxyethyl)-aminomethyl phosphonate, hydroxyalkyl esters of phosphorus acids, alkylphosphate oligomers, ammonium polyphosphate (APP), resorcinol diphosphate oligomer (RDP), phosphazene flame retardants or ethylenediamine diphosphate (EDAP).

14.2 Nitrogen containing flame retardants, for example melamine-based flame retardants, isocyanurates, polyisocyanurate, esters of isocyanuric acid, like tris-(2-hydroxyethyl) isocyanurate, tris(hydroxymethyl)isocyanurate, tris(3-hydroxy-n-propyl)isocyanurate, triglycidyl isocyanurate, melamine cyanurate, melamine borate, melamine phosphate, melamine pyrophosphate, melamine polyphosphate, melamine ammonium polyphosphate, melamine ammonium pyrophosphate, dimelamine phosphate, dimelamine pyrophosphate, benzoguanamine, allantoin, glycoluril, urea cyanurate, a condensation product of melamine from the series melem, melam, melon and/or a higher condensed compound or a reaction product of melamine with phosphoric acid or a mixture thereof.

14.3 Organohalogen flame retardants, for example polybrominated diphenyl oxide (DE-60F, Great Lakes), decabromodiphenyl oxide (DBDPO; Saytex 102E (®, Albemarle)), tris[3-bromo-2,2-bis(bromomethyl)propyl]phosphate (PB 370, (®, FMC Corp.)), tris(2,3-dibromopropyl)phosphate, chloroalkyl phosphate esters such as tris(chloropropyl)phosphate, tris(2,3-dichloropropyl)phosphate, tris(1,3-dichloro-2-propyl)phosphate (Fyrol FR 2 (RTM ICL)), oligomeric chloroalkyl phosphate, chlorendic acid, tetrachlorophthalic acid, tetrabromophthalic acid, poly-β-chloroethyl triphosphonate mixture, tetrabromobisphenol A-bis(2,3-dibromopropyl ether) (PE68), brominated epoxy resin, brominated aryl esters, ethylene-bis(tetrabromophthalimide) (Saytex BT-93 (®, Albemarle)), bis(hexachlorocyclopentadieno)cyclooctane (Declorane Plus (®, Oxychem)), chlorinated paraffins, octabromodiphenyl ether, hexachlorocyclopentadiene derivatives, 1,2-bis(tribromophenoxy)ethane (FF680), tetrabromobisphenol A (Saytex RB100 (®, Albemarle)), ethylene bis-(dibromonorbornanedicarboximide) (Saytex BN-451 (®, Albemarle)), bis-(hexachlorocycloentadeno)cyclooctane, PTFE, tris(2,3-dibromopropyl) isocyanurate or ethylene-bis-tetrabromophthalimide.

Some of the halogenated flame retardants mentioned above are routinely combined with an inorganic oxide synergist. Some of the halogentated flame retardants mentioned above can be used in combination with triaryl phosphates (such as the propylated, butylated triphenyl phosphates) and the like and/or with oligomeric aryl phosphates (such as resorcinol bis(diphenyl phosphate), bisphenol A bis(diphenyl phosphate), neopentylglycol bis(diphenyl phosphate)) and the like.

14.4 Inorganic flame retardants, for example aluminium trihydroxide (ATH), boehmite (AlOOH), magnesium dihydroxide (MDH), zinc borates, $CaCO_3$, organically modified layered silicates, organically modified layered double hydroxides, and mixtures thereof. In regard to the synergistic combination with halogenated flame retardants, the most common inorganic oxide synergists are zinc oxides, antimony oxides like $Sb_2O_3$ or $Sb_2O_5$ or boron compounds.

15. Other additives, for example plasticisers, lubricants, rheology additives, catalysts, flow-control agents, optical brighteners, antistatic agents and blowing agents.

Preferred is a composition, which comprises a component a), a component b) and as component c) a further additive.

Preferred is a composition, wherein the weight ratio of component b) to component c) is from 10:1 to 1:30, in particular from 4:1 to 1:20, especially from 2:1 to 1:10, and the overall amount of component b) and component c) is below 50% by weight of component a).

Preferred is a composition, which comprises as component c) a further additive, which is an antioxidant, an UV absorber, a hindered amine light stabilizer, a nickel compound, a metal deactivator, a phosphite or phosphonite, a hydroxylamine or amine N-oxide, a thiosynergist, a peroxide scavenger, a nucleating agent or a flame retardant.

Preferred is a composition, which comprises as component c) a further additive, which is a phenolic antioxidant, a phosphite or phosphonite, an acid scavenger, an aminic antioxidant or a flame retardant.

Preferred is a composition, which comprises as component c) a phenolic antioxidant.

Preferred is a composition, which comprises as component c) a phenolic antioxidant, which is an ester of 3-(3,5-di-tert-butyl-4-hydroxyphenyl)propionic acid.

Optionally, a composition comprising a component a), a component b) and a component c) contains as component d) a second further additive.

Preferred is a composition, which comprises a component a), a component b), as component c) a further additive and as component d) a second further additive.

Preferred is a composition, which comprises a component a), a component b), as component c) a further additive and as component d) a second further additive, wherein component d) is different to component c).

Preferred is a composition, wherein the weight ratio of component b) to component d) is from 10:1 to 1:30, in particular from 4:1 to 1:20, especially from 2:1 to 1:10, and wherein the overall amount of component b), component c) and component d) is below 50% by weight of component a).

Preferred is a composition, which comprises a component a), a component b), as component c) a further additive, which is a phenolic antioxidant, a phosphite or phosphonite, an acid scavenger, an aminic antioxidant or a flame retardant, and as component d) a second further additive.

Preferred is a composition, which comprises a component a), a component b), as component c) a further additive, which is a phenolic antioxidant, a phosphite or phosphonite, an acid scavenger, an aminic antioxidant or a flame retardant, and as component d) a second further additive, wherein component d) is different to component c).

Preferred is a composition, which comprises a component a), a component b), a component c) and a component d), wherein component c) and component d) are independently from each other a phenolic antioxidant, a phosphite or phosphonite, an acid scavenger, an aminic antioxidant or a flame retardant.

Preferred is a composition, which comprises a component a), a component b), a component c) and a component d), wherein component c) and component d) are independently from each other a phenolic antioxidant, a phosphite or phosphonite, an acid scavenger, an aminic antioxidant or a flame retardant, and wherein component d) is different to component c).

Preferred is a composition, which comprises a component a), a component b), a component c) a phenolic antioxidant and a component d), which is a phosphite or phosphonite, an acid scavenger, an aminic antioxidant or a flame retardant.

Preferred is a composition, which comprises a component a), a component b), as component c) a phenolic antioxidant, which is an ester of 3-(3,5-di-tert-butyl-4-hydroxy-phenyl)propionic acid, and a component d), which is a phosphite or phosphonite, an acid scavenger, an aminic antioxidant or a flame retardant.

Preferred is a composition, which comprises a component a), a component b), as component c) a phenolic antioxidant and as component d) a phosphite or phosphonite.

Preferred is a composition, which comprises a component a), a component b), as component c) a phenolic antioxidant and as component d) an aminic antioxidant.

Preferred is a composition, which comprises a component a), a component b), as component c) a phenolic antioxidant and as component d) a flame retardant.

A further embodiment of the invention relates to an article, which is made from a composition, which comprises a) an organic material susceptible to oxidative, thermal or light-induced degradation, which is a polymer, and b) a compound of the formula (I-1).

Preferred is an article, which is made from a composition, which comprises a) an organic material susceptible to oxidative, thermal or light-induced degradation, which is a polymer, and b) a stabilizer mixture [I-1/2/3] as defined above, a stabilizer mixture [I-1-II-1] as defined above, a stabilizer mixture [I-1-III-2] as defined above or a product [P-V-2/3] as defined above.

Preferred is an article, which is made from a composition, which comprises a) an organic material susceptible to oxidative, thermal or light-induced degradation, which is a polymer, and b) a stabilizer mixture [1-1/2/3] as defined above.

Preferred is an article, which is made from a composition, which comprises a) an organic material susceptible to oxidative, thermal or light-induced degradation, which is a polymer, and b) a stabilizer mixture [I-1-II-1] as defined above.

Preferred is an article, which is made from a composition, which comprises a) an organic material susceptible to oxidative, thermal or light-induced degradation, which is a polymer, and b) a stabilizer mixture [I-1-III-2] as defined above.

Preferred is an article, which is made from a composition, which comprises a) an organic material susceptible to oxidative, thermal or light-induced degradation, which is a polymer, and b) a product [P-V-2/3] as defined above.

The composition can be advantageously used for the preparation of various shaped articles. Examples for such an article are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike, trucks) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded or co-extruded plates, glazing for buildings (monolithic, twin or multiwall), aircraft, schools, extruded sheets, window film for architectural glazing, train, transportation, sanitary articles, and greenhouse.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags. Non-woven fabrics such as medical fabrics and related apparel, industrial apparel, outdoor fabrics, in-home furnishing and construction fabrics.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, foamed articles (cushions, mattresses, impact absorbers), foams, sponges, dish clothes, mats, garden chairs, stadium seats, tables, couches, toys, building kits (boards/figures/balls), playhouses, slides, and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

Preferred is an article, which is a film, pipe, profile, bottle, tank, container or fiber.

Preferred is an article, which is moulded. In particular, the moulding is effected by injection, blow, compression, roto-moulding, slush-moulding or extrusion.

The article can be rigid or flexible.

Preferred is an article, which is flexible and a foam.

Preferred is an article, which is flexible and a foam, and wherein component a) is a polyurethane.

Preferred is an article, which is flexible and a foam, wherein the polymer is a polyurethane and the composition comprises as component c) a flame retardant, especially an organohalogen flame retardant.

A further embodiment of the invention relates to a process for protection of an organic material susceptible to oxidative, thermal or light-induced degradation, i.e. component a), which comprises the step of incorporation into or application onto the organic material a compound of formula (I-1).

Preferred is a process, which comprises the step of incorporation into or application onto the organic material a stabilizer mixture [I-1/2/3] as defined above, a stabilizer mixture [I-1-II-1] as defined above, a stabilizer mixture [I-1-III-2] as defined above or a product [P-V-2/3] as defined above.

Preferred is a process, which comprises the step of incorporation into or application onto the organic material a stabilizer mixture [I-1/2/3] as defined above.

Preferred is a process, which comprises the step of incorporation into or application onto the organic material a stabilizer mixture [I-1-II-1] as defined above.

Preferred is a process, which comprises the step of incorporation into or application onto the organic material a stabilizer mixture [I-1-III-2] as defined above.

Preferred is a process, which comprises the step of incorporation into or application onto the organic material a product [P-V-2/3] as defined above.

The incorporation into or application onto an organic material of a component b) refers herein to a compound of the formula (I-1) or, if other compounds of the formulae (I-2), (I-3), (II-1), (II-2), (II-3), (III-2), (III-3), (IV-2), (IV-3), (X-1) or (XI-1) are present, to the compounds of the aforementioned formulae. This applies especially in case that component b) is a stabilizer mixture [1-1/2/3] as defined above, a stabilizer mixture [I-1-II-1] as defined above, a stabilizer mixture [I-1-III-2] as defined above or a product [P-V-2/3] as defined above.

The incorporation or application of component b) can be carried out in a processing apparatus, in particular a heatable container equipped with a stirrer, which can preferably be closed. A heatable container equipped with a stirrer is for example a kneader, extruder, mixer or stirred vessel. In the case of manufacturing polyurethane foam, component b) can be added into a mixing head, i.e. a specific type of mixer, where the other ingredients and starting materials are dosed. Specific examples for heatable containers equipped with a stirrer are a single-screw extruder, contrarotating and corotating twin-screw extruder, planetary-gear extruder, ring extruder or co-kneader. It is also possible to use a processing apparatus, which contains at least one gas removal compartment to which a vacuum can be applied and/or which can be set under an atmosphere, wherein the oxygen content is low or oxygen is absent. Component b) can be added directly into the processing apparatus.

Component b) can be incorporated or applied to at any stage of processing of component a), in particular prior to or during a shaping operation of component a) in the processing apparatus.

Component b) can be incorporated or applied in the form of a dry powder, in the form of a melt, in the form of an oil—wherein these three options depend on the specific properties of a specific component b)—, in encapsulated form such as encapsulation in a wax or polymer or in the form of a wet mixture such as a solution, dispersion or suspension for example in an inert solvent, water or oil. A dispersing or suspension agent can be present in the case of a wet mixture of component b).

Component b) can also be incorporated or applied by spraying onto component a).

In case that component a) is a polymer, a further possibility for incorporation or application of component b) to component a) is addition before, during or directly after the polymerization of the corresponding starting materials, e.g. monomers, of component a). For example, spraying during the deactivation of the polymerization catalysts is particularly advantageous. Another example is the incorporation into a polyol prior to the polycondensation of the polyol with an isocyanurate to polyurethane. If component a) is polymer and cross-linking takes place during formation of component a), incorporation or application prior to cross-linking is preferred.

In case that component a) is a polymer, the process of incorporation or application is preferably a moulding process, in particular an injection-moulding, blow-moulding, compression-moulding, roto-moulding, slush-moulding or extrusion-moulding.

The incorporation or application can take place at temperatures between 50° C. and 340° C. A typical temperature range for incorporation into a polyol is 60° C. to 90° C.

Preferred is a process, wherein the incorporation or application takes place at a temperature in the range from 150 to 340° C., in particular from 180° C. to 330° C., especially from 190° C. to 320° C.

Preferred is a process, wherein component b) is incorporated into or applied to component a), which is in particular a polymer, in an extruder during processing of component a).

Preferred is a process, wherein component b) is incorporated into or applied to component a), which is a polyurethane, in particular a polyurethane foam, in a mixing head, where other ingredients and starting materials are dosed.

In case of a further additive, i.e. component c) or components c) and d), component b) and the further additive, e.g. component c) or components c) and d), can be incorporated into or applied onto component a) individually or mixed with one another. If desired, the individual components can be mixed with one another before incorporation into component a) for example by dry blending, compaction, melting, encapsulation by a wax or polymer or as wet mixture in the form of solutions, dispersions or suspensions for example in an inert solvent, water or oil. Dependent on the specific components b) and c), or b), c) and d), their mixture can be liquid at 5 to 40° C., especially at 20° C., and a pressure of 500 to 1500 mbar (50 to 150 kPa).

Component b) and a further additive, e.g. component c) or component c) and component d), can also be added to component a) in the form of a masterbatch ('concentrate'), which contains the component b), the further additive, e.g. component c) or component c) and component d), and a masterbatch polymer. The component b) and a further additive, e.g. component c) or component c) and component d), are incorporated into the masterbatch in a concentration of, for example, from 1% to 40% and preferably 2% to 20% by weight of the masterbatch. The masterbatch polymer content is the difference towards 100% by weight of the masterbatch. In case that component a) is a polymer, the masterbatch polymer must not be necessarily the same type of polymer as component a).

A further embodiment to the invention relates to the use of a compound of the formula (I-1) for stabilizing an organic material susceptible to oxidative, thermal or light-induced degradation, i.e. component a), against degradation by oxidation, heat or light.

Preferred is a use of a stabilizer mixture [I-1/2/3] as defined above, a stabilizer mixture [I-1-II-1] as defined above, a stabilizer mixture [I-1-III-2] as defined above or a product [P-V-2/3] as defined above for stabilizing an organic material susceptible to oxidative, thermal or light-induced degradation, i.e. component a), against degradation by oxidation, heat or light.

Preferred is a use of a stabilizer mixture [I-1/2/3] as defined above for stabilizing an organic material susceptible to oxidative, thermal or light-induced degradation, i.e. component a), against degradation by oxidation, heat or light.

Preferred is a use of a stabilizer mixture [I-1-II-1] as defined above for stabilizing an organic material susceptible to oxidative, thermal or light-induced degradation, i.e. component a), against degradation by oxidation, heat or light.

Preferred is a use of a stabilizer mixture [I-1-III-2] as defined above for stabilizing an organic material susceptible to oxidative, thermal or light-induced degradation, i.e. component a), against degradation by oxidation, heat or light.

Preferred is a use of a product [P-V-2/3] as defined above for stabilizing an organic material susceptible to oxidative, thermal or light-induced degradation, i.e. component a), against degradation by oxidation, heat or light.

Preferred is the use of a compound of the formula (I-1) for stabilizing a foam, which contains polyurethane, against scorching.

Processing of a component a), especially if component a) is a polymer, is characterized as short-term exposure of the component a) to heat, for example to a temperature in the range of 150° C. to 340° C., during the time of processing of component a). The time of processing is short in comparison to for example the possible time of usage. Usage takes typically place at a temperature, for example 0° C. to 50° C., which is below the temperature during processing.

Preferred is the use of a compound of formula (I-1) for stabilizing a component a) against oxidative or thermal degradation during processing.

A further embodiment of the invention relates to a process for preparing a compound of the formula (I-1), which comprises the step of reacting a compound of the formula (V-2)

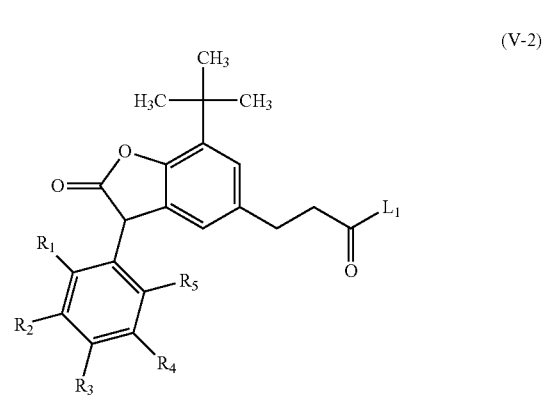

and a compound of the formula (V-3)

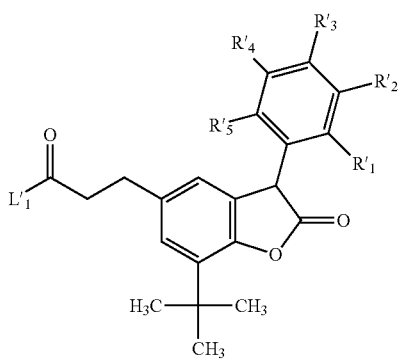

with a compound of the formula (VI)

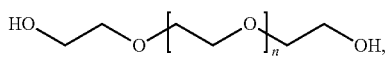

wherein n, $R_1$ to $R_5$ and $R'_1$ to $R'_5$ are defined as described at the embodiment of the compound of formula (I-1); and $L_1$ and $L'_1$ are each independently from each other hydroxy or $C_1$-$C_6$-alkyl-oxy.

The preferences and combination of preferences for n, $R_1$ to $R_5$, $R'_1$ to $R'_5$ and E, which are described at the embodiment of the compound of the formula (I-1), apply similarly to the process for preparing a compound of formula (I-1).

Preferably, the reacting takes place at a temperature between 5 and 200° C.

Preferably, the reacting takes place in the presence of a solvent, in particular in a solvent, which does not contain hydroxy groups.

Preferably, the reacting takes place in the presence of a catalyst, in particular an acidic catalyst and especially a solid acidic catalyst.

Preferably, the by-products $L_1$-H and $L'_1$-H are removed during reacting, in particular by application of a vacuum and/or distillation. Especially preferred is the co-distillation, in particular under vacuum, with a solvent, which is preferably returned to the reacting after separation from $L_1$-H and $L'_1$-H.

Preferably, the molar ratio between the summarized molar amounts of the compounds of the formulae (V-2) or (V-3) and the molar amount of the compound of the formula (VI) is from 1 to 3, especially 1.5 to 2.5 and in particular 1.8 to 2.2.

Preferred is a process for preparing a stabilizer mixture [I-1-II-1] containing
  b-I-1) a compound of the formula (I-1); and
  b-II-1) a compound of the formula (II-1);
which comprises the step of reacting a compound of the formula (V-2) and a compound of the formula (V-3) with a compound of the formula (VI) and a compound of the formula (VII); wherein n is an integer from 1 to 24.

Preferred is a process for preparing a stabilizer mixture [I-1-II-1], wherein the molar ratio between the summarized molar amounts of the compounds of the formulae (V-2) or (V-3) and the summarized molar amounts of the compounds of the formulae (VI) or (VII) is from 1 to 3, especially 1.5 to 2.5 and in particular 1.8 to 2.2.

Preferred is a process for preparing a product [P-V-2/3], which comprises the step of reacting a compound of the formula (V-2) and a compound of the formula (V-3) with a mixture of diols, which comprises
  m-VI) a compound of the formula (VI);
  m-VII) a compound of the formula (VII); and
  m-VIII) a compound of the formula (VIII);
wherein n is an integer from 1 to 23.

Preferred is a process for preparing a product [P-V-2/3], which comprises the step of reacting a compound of the formula (V-2) and a compound of the formula (V-3) with a mixture of diols, which comprises
  m-VI) a compound of the formula (VI);
  m-VII) a compound of the formula (VII);
  m-VIII) a compound of the formula (VIII); and
  m-IX) a compound of the formula (IX);
wherein n is an integer from 1 to 22.

Preferred is a process for preparing a product [P-V-2/3], wherein the molar ratio between the summarized molar amounts of the compounds of the formulae (V-2) or (V-3) and the summarized molar amounts of the diols is from 1 to 3, especially 1.5 to 2.5 and in particular 1.8 to 2.2.

The following examples illustrate further the invention without limiting it.

EXAMPLE 1

Preparation of Compound (101)

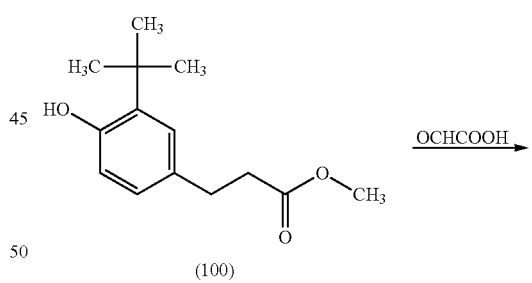

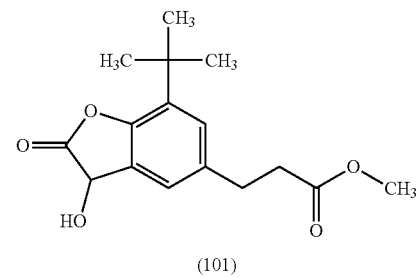

15 g of compound (100) (methyl 3-(3-tert-butyl-4-hydroxyphenyl)propionate), which is prepared in analogy to EP-A-

423070, is dissolved in 70 mL 1,2-dichloroethane, and 10.4 g glyoxylic acid (50% in water) as well as 0.445 g p-toluenesulfonic acid mono hydrate are added. The mixture is refluxed for 4 h at 83° C. 1,2-Dichloroethane is subsequently removed in vacuum. The crude product is dissolved in 100 mL methyl-tert-butyl ether and washed with water (3 times). The organic phase is dried over sodium sulfate and subsequently evaporated in vacuum. The obtained crude product is dried at 0.3 mbar and 60° C. to yield 18.6 g of a material containing compound (101).

$^1$H-NMR (400 MHz, CDCl$_3$): 5.03 (lactone).

$^{13}$C-NMR (100 MHz, CDCl$_3$): 175.6 (C=O), 173.0 (C=O), 67.7 (CHOH).

EXAMPLE 2

Preparation of Product (102)

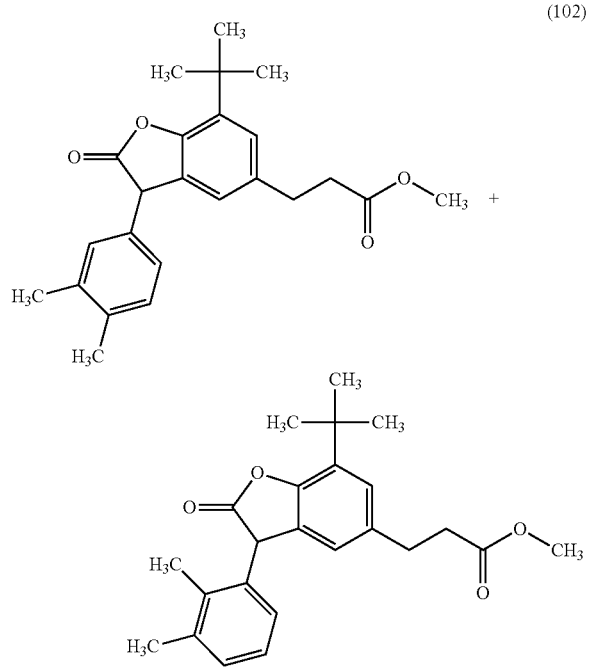

a) 4.5 g anhydrous aluminum(III)-chloride (Fluka Inc.) is suspended in 30 mL ortho-xylene and cooled to 0° C. 5.0 g compound (101) prepared according to example 1 is dissolved in 15 mL ortho-xylene and afterwards added over a period of 50 min. After that, stirring is continued for 2 h. The temperature is increased stepwise to 40° C. After 14 h, further anhydrous 1.5 g aluminum(III)-chloride is added at 40° C. and stirring is continued for 5 h at 40° C. Crude ice is added at 0° C., followed by 37% aqueous HCl until a pH value of 0 is reached. The aqueous phase is extracted twice with in methyl-tert-butyl ether. The organic phase is washed with sodium carbonate solution and twice with water. After drying over sodium sulfate, the organic solvent is removed in vacuum to yield 5.5 g red oil. The crude product is purified via flash chromatography (silicagel; hexane/ethyl acetate gradient solvent system) to afford 2.9 g product (102) as a mixture of the 3,4- and 2,3-isomers.

$^1$H-NMR (400 MHz, CDCl$_3$): 4.77 (lactone).

$^{13}$C-NMR (75 MHz, CDCl$_3$): 175.7, 173.1, 150.4, 137.5-122.4 (m), 51.6, 49.2, 36.0, 34.3, 30.9, 29.6, 19.8, 19.4.

M.p.: 70.5-72.4° C. (mixture of 3,4- and 2,3-isomers)

b) 8.4 g glyoxylic acid (50% in water) and 50 mL ortho-xylene are mixed in a reactor. The mixture is heated to 90° C., while a vacuum of 200 mbar is applied, and water is distilled-off from the reaction mixture using a Dean-Stark apparatus. Within 20 min, approximately 3.5 mL of water are removed. 10.0 g of compound (101) prepared according to example 1 is added, followed by 0.445 g p-toluenesulfonic acid monohydrate. The reaction mixture is refluxed at 250 mbar and a temperature of 105° C. for 40 min. 1.4 g Fulcat 22B (acid-activated Montmorillonite clay catalyst, offered for instance by Rockwood Additives Limited, Cheshire, UK) is added and refluxing is continued for 4 h at 200 mbar. Then, the catalyst is removed by filtration. The organic phase is washed with sodium carbonate solution and twice with water. After drying over sodium sulphate, the organic solvent is removed under vacuum. A material containing product (102) as a mixture of 3,4- and 2,3-isomers is obtained (brown, viscous oil; 13.7 g).

c) 330.5 g of compound (101) prepared in analogy to example 1 is dissolved in 1557 mL ortho-xylene and 32.6 mL methanesulfonic acid (99.5%) is added. The reaction mixture is heated to 95-105° C. under vacuum and water is distilled-off using a Dean-Stark apparatus. After 2 hours of heating, approximately 10 mL of water is removed. Heating is continued for another 0.5 hours. The reaction mixture is cooled to ambient temperature and 200 mL saturated aqueous sodium hydrogencarbonate solution is added. After neutralization of the methanesulfonic acid, the phases are separated, and the organic phase is washed with water (300 mL) and brine. The organic phase is dried over sodium sulphate, filtered, and the organic solvent is removed in vacuo. 304 g crude product (102) is obtained as red oil. The compound is purified by repetitive crystallization from methanol and methanol/hexane. Remaining product in the crystallization filtrates is subsequently isolated through flash chromatography (silica gel; hexane/ethyl acetate gradient solvent system). Product (102) is obtained in a combined yield of 250.1 g as a mixture of 3,4- and 2,3-isomers.

d) 8.4 g glyoxylic acid (50% in water) and 50 mL ortho-xylene are mixed in a reactor. The mixture is heated to 95° C., while a vacuum of 280 mbar is applied. Using a Dean-Stark apparatus, approximately 3 mL of water are removed in 1 hour. 10.0 g of compound (101) prepared in analogy to example 1, 0.3 g p-toluenesulfonic acid monohydrate and 1.4 g Fulcat 22B (acid activated Montmorillonite clay catalyst, offered for instance by Rockwood Additives Limited, Cheshire, UK) are added. The reaction mixture is refluxed at 280 mbar and 97° C. The reaction progress is followed by gas chromatography. After 5 h, the residual amounts of compound (100) and compound (101) are below 1%. Product (102) is obtained in 57% yield.

EXAMPLE 3A

Preparation of Stabilizer Product (103)

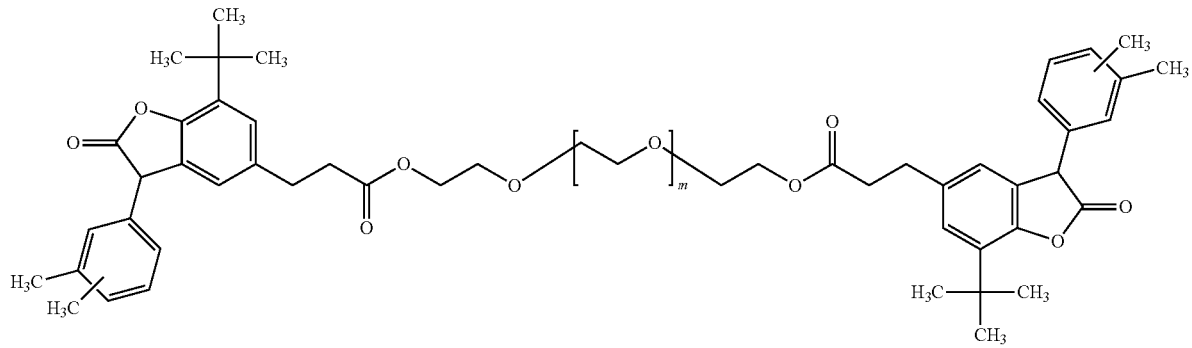

m = mainly 2 or 3

249.1 g of product (102) prepared according to example 2c) (calculated as 0.655 mol) and 81.3 g polyethylene glycol 200 (PEG 200; average molecular weight 200; Fluka Inc.; calculated as 0.406 mol) are separately co-distilled with cyclohexane to remove traces of water. In a reactor, PEG 200 is stirred under vacuum at 450 mbar and a temperature of 120° C. for 30 min and then for 10 min at 3 mbar. Under inert argon atmosphere, product 102 is added, followed by 2.68 g aluminium triisopropylate (98%, Aldrich Inc.; 0.0131 mol). The reactor is evacuated twice to 100 mbar and ventilated with argon. Vacuum is set to 280 mbar and the temperature is adjusted to 145° C. over a period of 30 min. After 1 hour of stirring, the vacuum is lowered to 3 mbar over 30 min. After another 1 hour, further 1.34 g aluminium triisopropylate (0.0066 mol) is added. After 16 hours of stirring, the temperature is increased to 155° C. and another 2.68 g aluminiumtriisopropylate (0.0131 mol) is added. Stirring is continued for another 7.5 h. At this time, the amount of remaining product (102) is approximately 2.8% as determined by HPLC. After cooling to 85° C., 8.8 g aqueous citric acid solution (50%) is added and stirring is continued for 20 min. Then, 180 g of water are added at 75° C. The reaction mixture is subsequently extracted with 500 mL ethyl acetate. To facilitate phase separation, 180 mL methyl-tert-butyl ether is added, followed by ethanol until the organic phase becomes clear. The organic phase is washed twice with brine and then dried over sodium sulphate. After removal of the organic solvent, the crude product is dried in vacuum (2 mbar, 60° C.) to afford 302.4 g oil, which contains product (103). Analytical data for oil containing product (103):

$^1$H-NMR (400 MHz, CDCl$_3$): 7.27-6.76 (m), 5.27, 4.74, 4.19 (m), 3.65-3.59 (m), 2.92-2.87 (m), 2.63-2.58 (m), 2.34, 2.24, 1.42.

$^{13}$C-NMR (100 MHz, CDCl$_3$): 175.1, 172.6, 150.4, 137.9-122.1 (m), 70.6, 70.5, 69.2, 69.1, 69.0, 63.6, 63.5, 63.4, 53.5, 49.2, 36.0, 34.3, 29.6, 29.4, 21.5, 20.9, 19.8, 19.5.

ATR-IR (major peaks, cm$^{-1}$): 2956, 2870, 1800, 1731, 1422, 1189, 1069, 904.

EXAMPLE 3B

Preparation of Stabilizer Product (104)

(104)

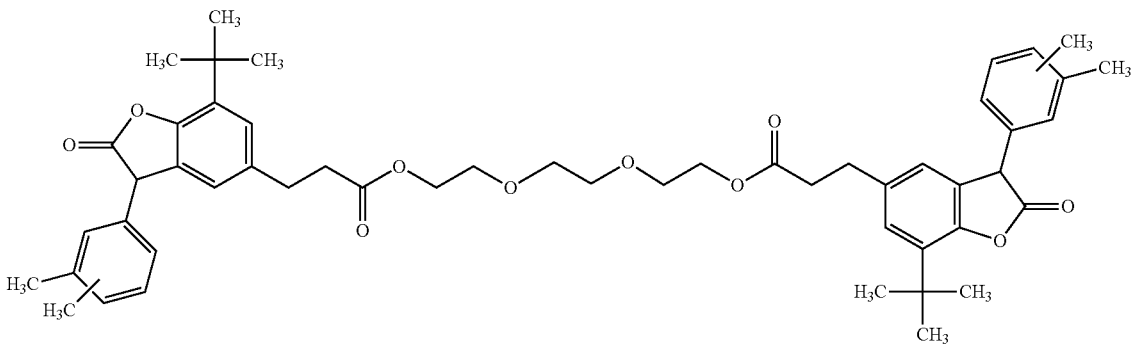

A synthetic preparation is conducted similar like at example 3a) using triethylene glycol as diol component. The product (104) is isolated after flash chromatography (silica gel; heptane/ethyl acetate (8:2)) as a yellow oil in 30% yield.

$^1$H-NMR (400 MHz, CDCl$_3$)—characteristic signals: 4.77 (s, 2H, lactone H), 4.22 (m, 4H), 3.67 (m, 4H), 2.92 (m, 4H), 2.63 (m, 4H), 2.27 (s, 6H).

$^{13}$C-NMR (100 MHz, CDCl$_3$)—characteristic signals: 175.7, 172.6, 150.4, 70.5, 69.2, 63.5, 49.2, 19.8, 19.4.

EXAMPLE 3C

Preparation of Stabilizer Product (105)

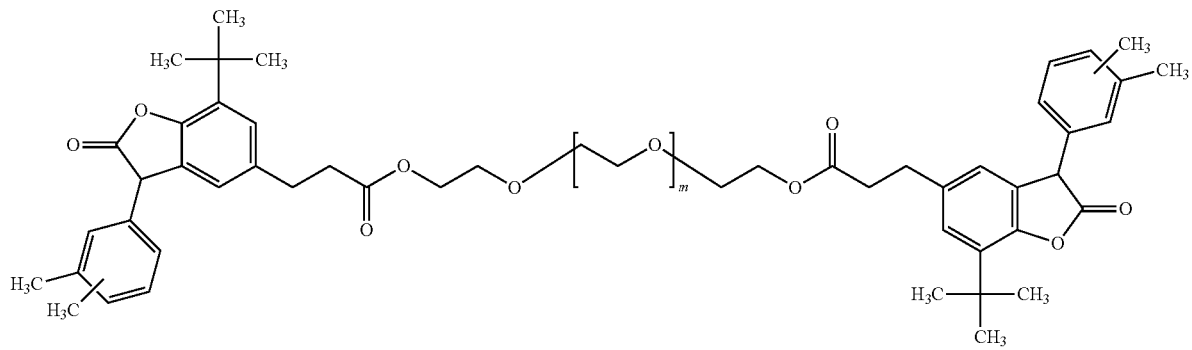

m = 2

A synthetic preparation is conducted similar like at example 3a) with tetraethylene glycol as diol component. After removal of the organic solvent, the crude product is dried in vacuum (2 mbar, 60° C.) to afford a yellow oil in 38% yield, which contains product (105).

$^{1}$H-NMR (400 MHz, CDCl$_{3}$)—characteristic signals: 4.77 (s, 2H, lactone H), 4.21 (m, 4H), 3.65 (m, 12H), 2.92 (m, 4H), 2.62 (m, 4H), 2.27 (s, 6H).

$^{13}$C-NMR (100 MHz, CDCl$_{3}$)—characteristic signals: 175.7, 172.6, 150.4, 70.6, 70.5, 69.1, 49.2, 19.8, 19.4.

EXAMPLE 3D

Preparation of Stabilizer Product (106)

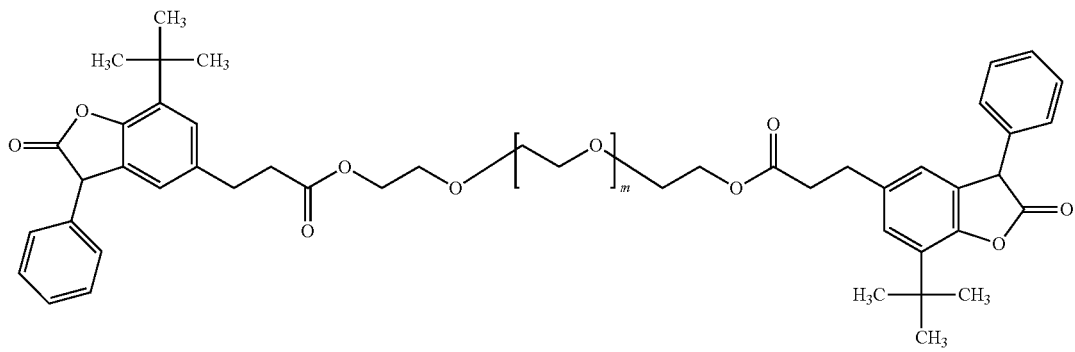

m = mainly 2 or 3

A synthetic preparation is conducted according to WO-A-2000/23849, example 11, using PEG 200 as diol component. After solvent removal, the crude product is dried in vacuum (2 mbar, 60° C.) to afford a yellow oil in 80% yield which contains product (106).

$^{1}$H-NMR (400 MHz, CDCl$_{3}$)—characteristic signals: 4.84 (s, 2H, lactone H), 4.21 (m, 4H), 3.65 (m, 14H), 2.93 (m, 4H), 2.62 (m, 4H).

$^{13}$C-NMR (100 MHz, CDCl$_{3}$): 175.3, 172.7, 150.4, 64.4, 49.5.

EXAMPLE 3E

Preparation of Stabilizer Product (107)

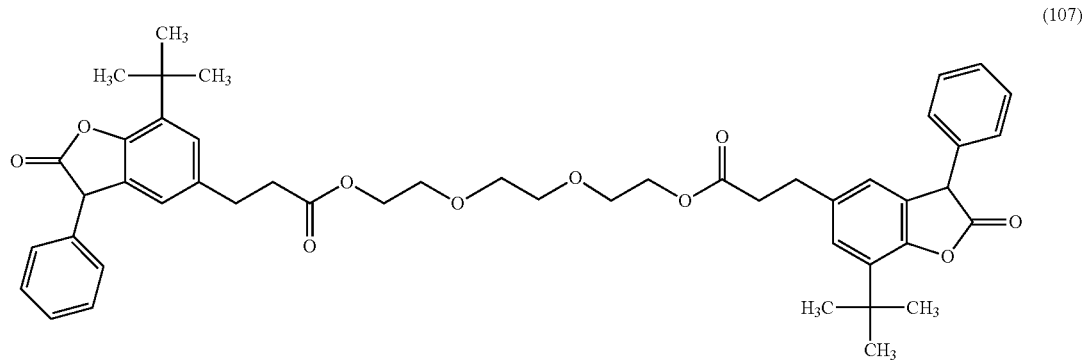 [SMILES: CC(C)(C)c1cc(CCC(=O)OCCOCCOCCOC(=O)CCc2cc3c(c(C(C)(C)C)c2)OC(=O)C3c2ccccc2)cc2c1OC(=O)C2c1ccccc1]

A synthetic preparation is conducted according to WO-A-2000/23849, example 11, using triethylene glycol as diol compound. The product (107) is isolated after flash chromatography (silica gel; hexane/ethyl acetate gradient solvent system) as a yellow oil in approximately 10% yield.

$^1$H-NMR (400 MHz, CDCl$_3$)—characteristic signals: 4.84 (s, 2H, lactone H), 4.21 (m, 4H), 3.65 (m, 8H), 2.93 (m, 4H), 2.61 (m, 4H).

$^{13}$C-NMR (100 MHz, CDCl$_3$)—characteristic signals: 175.4, 172.6, 150.4, 70.5, 69.2, 64.4, 49.5, 36.0, 34.3, 30.8.

EXAMPLE 3F

Preparation of Stabilizer Product (108)

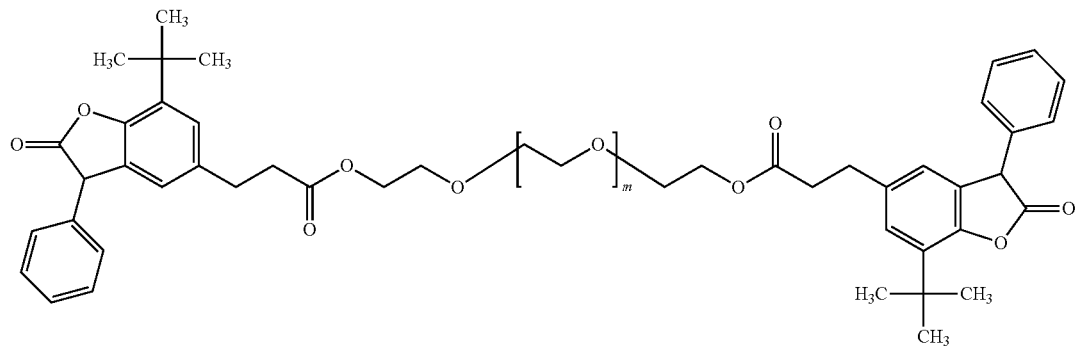

m = 2

A synthetic preparation is conducted according to WO-A-2000/23849, example 11, using tetraethylene glycol as diol compound. The product (108) is isolated after flash chromatography (silica gel; methylene chloride/ethyl acetate (40:1)) as a yellow oil in approximately 24% yield.

$^1$H-NMR (400 MHz, CDCl$_3$)—characteristic signals: 4.84 (s, 2H, lactone H), 4.21 (m, 4H), 3.65 (m, 12H), 2.93 (m, 4H), 2.62 (m, 4H).

$^{13}$C-NMR (100 MHz, CDCl$_3$)—characteristic signals: 175.4, 172.6, 150.4, 70.6, 69.1, 63.6, 49.5.

EXAMPLE 4

Stabilization of a Polyol

The oxidation resistance of the tested polyol is determined by differential scanning calorimetry (DSC). A sample is heated starting at 50° C. with a heating rate of 5° C./min under oxygen until 200° C. is reached. The appearance of an exothermic peak indicates the beginning of a thermo-oxidative reaction. The temperature at the onset of the exothermic peak is noted. A better stabilized sample is characterized by a higher temperature for the onset.

Lupranol 2084 (RTM BASF) is a trifunctional polyether polyol, which contains predominantly secondary hydroxyl groups and which possess a hydroxyl number 48 mg KOH/g, a water content less than 0.1% and an acid number less than 0.06 mg KOH/g.

Irganox 1135 (RTM BASF) is a phenolic antioxidant and contains 3-(3,5-di-tert-butyl-4-hydroxy-phenyl)-propionic acid iso-octyl ester as depicted:

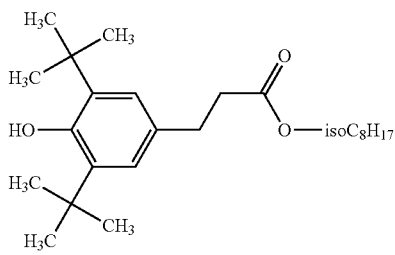
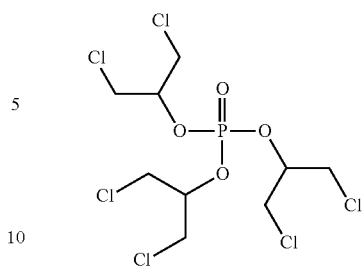

Irganox 5057 (RTM BASF) is an aminic antioxidant and is a technical mixture obtained by the reaction of diphenylamine with diisobutylene, comprising α) diphenylamine;
β) 4-tert-butyldiphenylamine;
χ) compounds of the group
  i) 4-tert-octyldiphenylamine,
  ii) 4,4'-di-tert-butyldiphenylamine,
  iii) 2,4,4'-tris-tert-butyldiphenylamine,
δ) compounds of the group
  i) 4-tert-butyl-4'-tert-octyldiphenylamine,
  ii) o,o', m,m', or p,p'-di-tert-octyldiphenylamine,
  iii) 2,4-di-tert-butyl-4'-tert-octyldiphenylamine,
ε) compounds of the group
  i) 4,4'-di-tert-octyldiphenylamine,
  ii) 2,4-di-tert-octyl-4'-tert-butyldiphenylamine, and wherein not more than 5% by weight of component α), 8 to 15% by weight of component β), 24 to 32% by weight of component χ), 23 to 34% by weight of component δ) and 21 to 34% by weight of component ε) are present.

100 parts of Lupranol 2084 (RTM BASF; polyol) are admixed with 0.45 parts of a stabilizer composition, which consists of Irganox 1135 (RTM BASF; 0.32 parts based on 100 parts of polyol), Irganox 5057 (RTM BASF; 0.10 parts based on 100 parts of polyol) and a stabilizer product according to the invention (0.03 parts of material obtained in an example based on 100 parts of polyol).

TABLE 1

| No. | tested sample | temperature of onset [° C.] |
|---|---|---|
| 4-1[a] | 100 parts polyol without stabilizer composition | 133 |
| 4-2[b] | 100 parts polyol with 0.45 parts stabilizer composition containing material obtained in example 3a) | 193 |

[a] comparative
[b] according to the invention

EXAMPLE 5

Stabilization of a Polyol Containing a Flame Retardant

The oxidation resistance of the tested polyol is determined by differential scanning calorimetry (DSC) as described in example 4.

Fyrol FR 2 (RTM ICL) is a liquid chlorinated flame retardant and contains tris-(1,3-dichloro-2-propyl phosphate) as depicted:

100 parts of Lupranol 2084 (RTM BASF; polyol) are admixed with 16 parts of Fyrol FR 2 (RTM ICL), 0.45 parts of a stabilizer composition, which consists of Irganox 1135 (RTM BASF; 0.32 parts based on 100 parts of polyol), Irganox 5057 (RTM BASF; 0.10 parts based on 100 parts of polyol) and of a stabilizer product according to the invention (0.03 parts of the material obtained in an example based on 100 parts of polyol).

TABLE 2

| No. | tested sample | temperature of onset [° C.] |
|---|---|---|
| 5-1[a] | 100 parts polyol without Fyrol FR 2 and without stabilizer composition | 127 |
| 5-2[a] | 100 parts polyol with Fyrol FR 2 and without stabilizer composition | 128 |
| 5-3[b] | 100 parts polyol with Fyrol FR 2 and with stabilizer composition containing material obtained in example 3a) | 194 |

Footnotes at table 1

EXAMPLE 6

Stabilization of a Polyether/Polyurethane Soft Foam

Preparation of Polyether/Polyurethane Soft Foams 0.71 g of a stabilizer composition (0.45 parts based on 100 parts of polyol), which consists of Irganox 1135 (RTM BASF; phenolic antioxidant; 0.32 parts based on 100 parts of polyol), Irganox 5057 (RTM BASF; aminic antioxidant; 0.10 parts based on 100 parts of polyol) and a stabilizer product according to the invention (0.03 parts of the material obtained in an example based on 100 parts of polyol), is dissolved in 157.1 g Lupranol 2084 (RTM BASF). 9.84 g of a solution consisting of 1.88 g Tegostab BF 2370 (RTM Evonik Industries; surfactant based on polysiloxane), 0.24 g Tegoamin 33 (RTM Evonik Industries; general purpose gelling catalyst based on triethylene diamine) and 7.7 g of deionized water are added and the reaction mixture is stirred vigorously for 10 seconds at 2600 rpm. 0.31 g Kosmos 29 (RTM Evonik Industries; catalyst based on stannous octoate) is then added and the reaction mixture is again stirred vigorously for 18 seconds at 2600 rpm. 92.19 g of Lupranat T80 (RTM BASF; toluene-2, 4- and toluylene-2,6-diisocyanate mixture) is then added with continuous stirring for 5 to 7 seconds at 2600 rpm. The mixture is then poured into a 20×20×20 cm cake-box and an exothermic foaming reaction takes place as indicated by an increase of temperature. The foam blocks are cooled and stored at room temperature for 24 hours.

All prepared foam blocks show a comparable initial white colour.

Anti-Scorch Testing

Scorch resistance is determined by static heat aging, i.e. static alu-block test. The foam blocks are cut into thin tubes (2 cm thick, 1.5 cm in diameter). From each foam block, a thin tube is taken as foam sample. The foam sample is heated in an aluminum block. The temperature is kept for 30 min at the temperatures of 180, 190, 200 and 210° C. The scorch resistance is assessed by measuring the colour of the foam sample after aging. The measured colour is reported in terms of Yellowness Index (YI) determined on the foam sample in accordance with the ASTM 1926-70 Yellowness Test. Low YI values denote little discoloration, high YI values severe discoloration of the samples. The whiter a foam sample remains, the better the foam sample is stabilized.

TABLE 3

| No. | tested sample | YI after 30 min exposure at 180° C. | YI after 30 min exposure at 190° C. | YI after 30 min exposure at 200° C. | YI after 30 min exposure at 210° C. |
| --- | --- | --- | --- | --- | --- |
| 6-1[a] | 100 parts polyol without stabilizer composition | 19.5 | 25.1 | 45.7 | 54.1 |
| 6-2[b] | 100 parts polyol with 0.45 parts stabilizer composition containing material obtained in example 3a) | −1.1 | −2.3 | 3.9 | 24.7 |

Footnotes at table 1

EXAMPLE 7

Stabilization of Polyether/Polyurethane Soft Foam Containing a Flame Retardant

Preparation of Polyether/Polyurethane Soft Foams Containing a Flame Retardant 0.71 g of a stabilizer composition (0.45 parts based on 100 parts of polyol), which consists of Irganox 1135 (RTM BASF; phenolic antioxidant; 0.32 parts based on 100 parts of polyol), Irganox 5057 (RTM BASF; aminic antioxidant; 0.10 parts based on 100 parts of polyol) and a stabilizer product according to the invention (0.03 parts of material obtained in an example based on 100 parts of polyol), is dissolved in 157.1 g Lupranol 2084 (RTM BASF). 25.14 g of Fyrol FR 2 (RTM ICL; tris-(1,3-dichloro-2-propyl phosphate); 9.84 g of a solution consisting of 1.88 g Tegostab BF 2370 (RTM Evonik Industries; surfactant based on polysiloxane), 0.24 g Tegoamin 33 (RTM Evonik Industries; general purpose gelling catalyst based on triethylene diamine) and 7.7 g of deionized water are added and the reaction mixture is stirred vigorously for 10 seconds at 2600 rpm. 0.31 g Kosmos 29 (RTM Evonik Industries; catalyst based on stannous octoate) is then added and the reaction mixture is again stirred vigorously for 18 seconds at 2600 rpm. 92.19 g of Lupranat T80 (RTM BASF; toluene-2,4- and toluylene-2,6-diisocyanate mixture) is then added with continuous stirring for 5 to 7 seconds at 2600 rpm. The mixture is then poured into a 20×20×20 cm cake-box and an exothermic foaming reaction takes place as indicated by an increase of temperature. The foam blocks are cooled and stored at room temperature for 24 hours.

All prepared foam blocks show a comparable initial white colour.

Anti-scorch test is carried out according to the method described in Example 6.

TABLE 4

| No. | tested sample | YI after 30 min exposure at 180° C. | YI after 30 min exposure at 190° C. | YI after 30 min exposure at 200° C. | YI after 30 min exposure at 210° C. |
| --- | --- | --- | --- | --- | --- |
| 7-1[a] | 100 parts polyol without stabilizer composition | 35.6 | 48.3 | 60.1 | 68.6 |
| 7-2[b] | 100 parts polyol with 0.45 parts stabilizer composition containing material obtained in example 3a) | 2.8 | 10.9 | 32.7 | 55.7 |

Footnotes at table 1

EXAMPLE 8

Stabilization of Polypropylene

The employed mini-extruder, which is commercially available from DSM, enables a flow of the melted polymer in a circle, i.e. two screws in a twin-screw arrangement press the melted polymer to the outlet, which is connected to the inlet zone of the extruder. The temperature of the steel barrel of the mini-extruder can be regulated and the inlet zone of the extruder can be purged with a gas, which allows the removal of entrapped air originating from the loading of the polymer sample. Furthermore, a sensor determines the force, which is exerted by the melted polymer onto the barrel during rotation of the two screws. A change in the viscosity of the melted polymer leads to a change of the force.

Tetra kis-[3-(3,5-di-tert-butyl-4-hydroxy-phenyl)-propionyloxymethyl]-methane is a phenolic antioxidant, which is contained for example in Irganox 1010 (RTM BASF), as depicted:

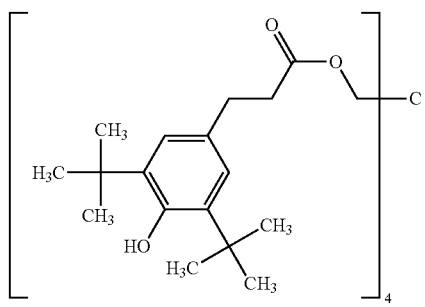

1,3,5-Tri-(2,6-tert-butyl-4-hydroxybenzyl)-2,4,6-trimethylbenzene is a phenolic antioxidant, which is contained for example in Irganox 1330 (RTM BASF), as depicted:

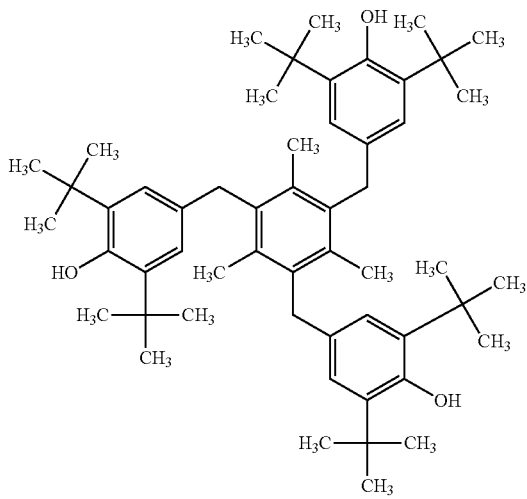 [SMILES: Cc1c(Cc2cc(C(C)(C)C)c(O)c(C(C)(C)C)c2)c(C)c(Cc2cc(C(C)(C)C)c(O)c(C(C)(C)C)c2)c(C)c1Cc1cc(C(C)(C)C)c(O)c(C(C)(C)C)c1]

Tris-(2,4-di-tert-butylphenyl)phosphite is a phosphite stabilizer, which is contained for example in Irgafos 168 (RTM BASF), as depicted:

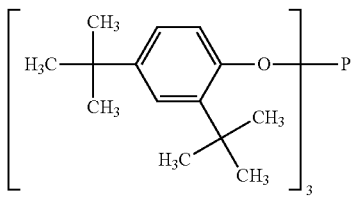

The steel housing of the extruder is set at a temperature of 280° C. and the inlet zone is set under a nitrogen flow of 20 mL/min. At a screw speed of 50 rpm, 9 g of a mixture, which consists of 8.955 g of a pipe grade polypropylene random copolymer (99.95% of the overall mixture) and 0.0045 g of a stabilizer product according to the invention (0.05% material obtained in an example of the overall mixture) are loaded. Said polypropylene random copolymer itself already contains 0.2% tetrakis-[3-(3,5-di-tert-butyl-4-hydroxy-phenyl)-propionyloxymethyl]-methane, 0.2% 1,3,5-tri-(2,6-tert-butyl-4-hydroxybenzyl)-2,4,6-trimethylbenzene, 0.1% tris-(2,4-di-tert-butylphenyl)phosphite and 0.05% calcium stearate.

After loading, the screw speed is set to 100 rpm and the force exerted on the barrel is recorded. The test is conducted for 10 min under nitrogen at a flow rate of 20 mL/min. After a short period, a steady decrease of the force is recorded. The decrease of the force is quantified as slope of the force-to-time curve, wherein the slope is calculated between the time period of 7 and 10 minutes. The curve is rather linear during said period. The decrease of the force with time is taken as degree of melt-degradation of the polymer sample.

Desired is a minimum of degradation, which is expressed by a small value for the slope of the curve. No degradation would mean zero slope. The results are shown in table 5.

TABLE 5

| No. | tested sample | slope under nitrogen atmosphere | slope under air atmosphere |
|---|---|---|---|
| 8-1[a)] | polymer without addition of a product according to the invention | −0.50 | −1.21 |
| 8-2[b)] | polymer with addition of material obtained in example 3a) | −0.29 | −0.59 |

Footnotes at table 1

The invention claimed is:

1. A compound of the formula (I-1)

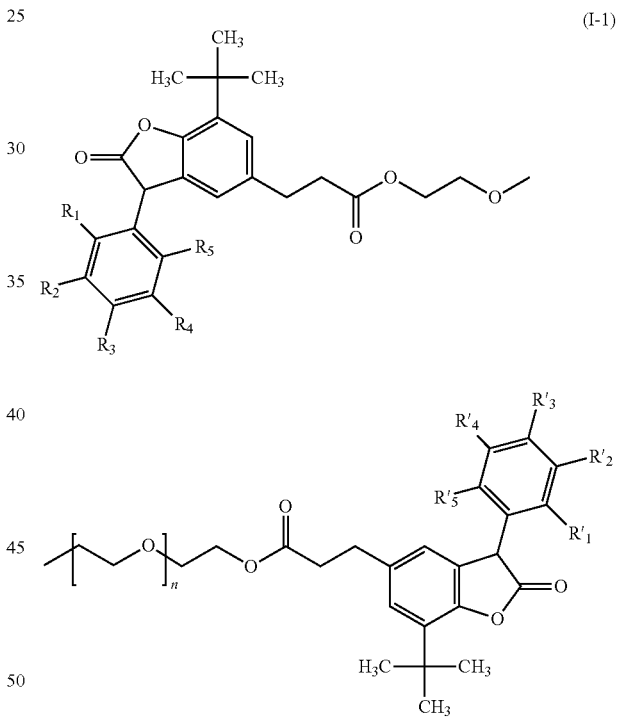

wherein n is 1, 2, 3, 4, 5, 6, 7, 8, 9, 10, 11, 12, 13, 14, 15, 16, 17, 18, 19, 20, 21, 22, 23, 24 or 25, $R_1$, $R_2$, $R_3$, $R_4$, $R_5$, $R'_1$, $R'_2$, $R'_3$, $R'_4$ and $R'_5$ are each independently selected from H or $C_1$-$C_8$-alkyl.

2. The compound according to claim 1, wherein a substituent R of $R_1$ to $R_5$ is different from a substituent R' of $R'_1$ to $R'_5$.

3. The compound according to claim 1, wherein $R_1$ or $R_5$ is H, and $R'_1$ or $R'_5$ is H.

4. The compound according to claim 1, wherein n is 1 to 9, and $R_1$, $R_2$, $R_3$, $R_4$, $R_5$, $R'_1$, $R'_2$, $R'_3$, $R'_4$ and $R'_5$ are each independently selected from H, $C_1$-$C_4$-alkyl or $C_8$-alkyl.

5. A stabilizer mixture, comprising:
at least one compound of formula (I-1)

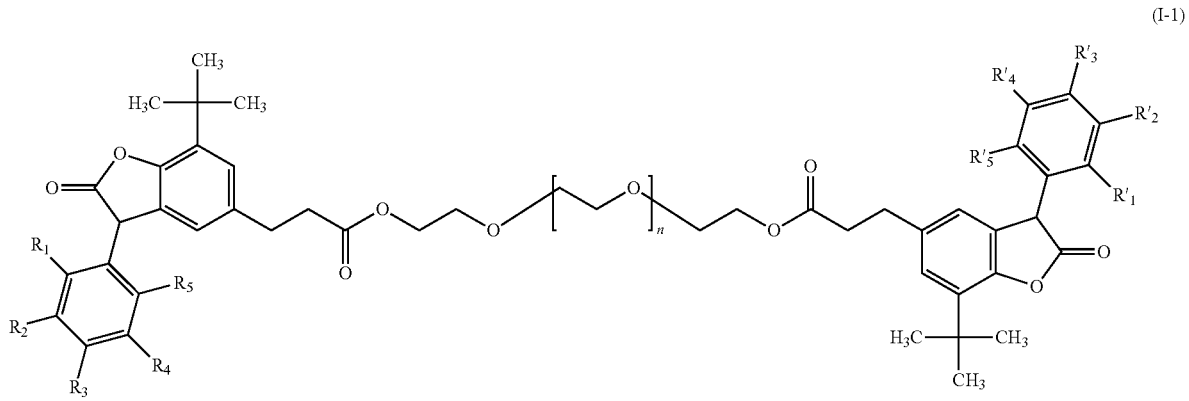

wherein n is an integer from 1 to 24,
$R_1$, $R_2$, $R_3$, $R_4$, $R_5$, $R'_1$, $R'_2$, $R'_3$, $R'_4$ and $R'_5$ are each independently selected from H or $C_1$-$C_8$-alkyl; and
at least one compound of formula (II-1)

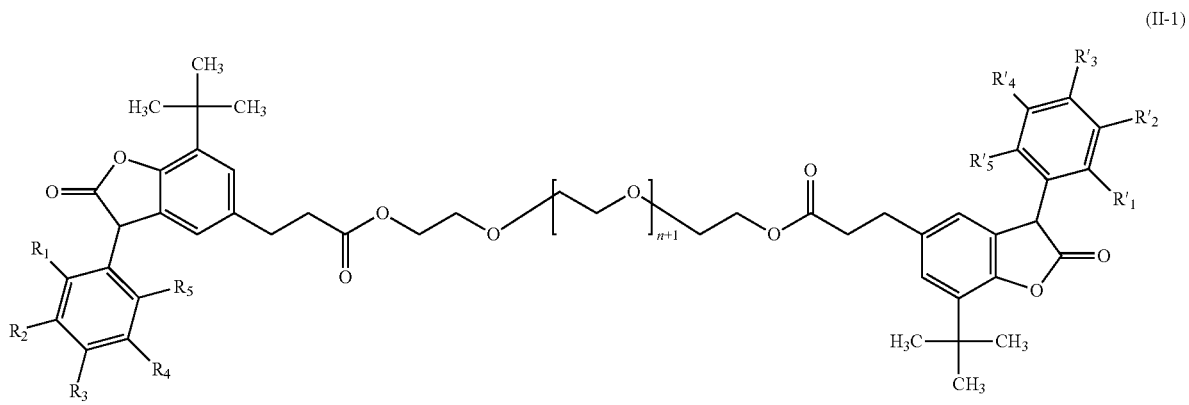

wherein n is an integer from 1 to 24; and
$R_1$, $R_2$, $R_3$, $R_4$, $R_5$ and $R'_1$, $R'_2$, $R'_3$, $R'_4$, $R'_5$ are as defined in claim 1.

6. A composition, which comprises
a) an organic material susceptible to oxidative, thermal or light-induced degradation; and
b) the compound of the formula (I-1) as defined in claim 1.

7. The composition according to claim 6, wherein the organic material is a polymer, which is semi-synthetic or synthetic.

8. The composition according to claim 6, wherein component a) is a polymer, which is a polyolefin, a polyether polyol or a polyurethane.

9. The composition according to claim 6, wherein component b) is present in an amount of 0.0001% to 10% based on the weight of component a).

10. The composition according to claim 6, further comprising: c) an additive.

11. The composition according to claim 10, wherein the additive is at least one selected from the group consisting of a phenolic antioxidant, a phosphite, a phosphonite, an acid scavenger, an aminic antioxidant and a flame retardant.

12. The composition according to claim 10, wherein a weight ratio of component b) to component c) is from 4:1 to 1:20.

13. The composition according to claim 10, which comprises two additives.

14. A process for protecting an organic material susceptible to oxidative, thermal or light-induced degradation, comprising incorporating or applying the compound of the formula (I-1) according to claim 1 into or onto the organic material.

* * * * *